US008993227B2

(12) United States Patent
Zhu et al.

(10) Patent No.: US 8,993,227 B2
(45) Date of Patent: Mar. 31, 2015

(54) CANCER PROGNOSIS BY DETERMINING PHOSPHORYLATION OF A XOM POLYPEPTIDE

(71) Applicants: Zhenglun Zhu, Allston, MA (US); Hong Gao, Allston, MA (US)

(72) Inventors: Zhenglun Zhu, Allston, MA (US); Hong Gao, Allston, MA (US)

( * ) Notice: Subject to any disclaimer, the term of this patent is extended or adjusted under 35 U.S.C. 154(b) by 0 days.

(21) Appl. No.: 13/859,285

(22) Filed: Apr. 9, 2013

(65) Prior Publication Data
US 2013/0280261 A1 Oct. 24, 2013

Related U.S. Application Data

(60) Continuation of application No. 13/206,003, filed on Aug. 9, 2011, now abandoned, which is a division of application No. 11/677,828, filed on Feb. 22, 2007, now Pat. No. 7,994,126.

(60) Provisional application No. 60/775,645, filed on Feb. 22, 2006.

(51) Int. Cl.
| | | |
|---|---|---|
| *C12Q 1/00* | (2006.01) | |
| *C12Q 1/68* | (2006.01) | |
| *G01N 33/53* | (2006.01) | |
| *C07K 14/46* | (2006.01) | |
| *C07K 14/47* | (2006.01) | |
| *A61K 38/00* | (2006.01) | |

(52) U.S. Cl.
CPC ............ *C12Q 1/6886* (2013.01); *C07K 14/463* (2013.01); *C07K 14/4702* (2013.01); *A61K 38/00* (2013.01)
USPC .................. 435/4; 435/6.1; 435/7.1; 435/7.5; 435/7.92

(58) Field of Classification Search
None
See application file for complete search history.

(56) References Cited

U.S. PATENT DOCUMENTS 6,544,962 B1   4/2003   Jones et al.

FOREIGN PATENT DOCUMENTS

| WO | WO01/75067 | 10/2001 |
| WO | WO2004/076622 | 9/2004 |
| WO | WO 2005/010180 | 2/2005 |

OTHER PUBLICATIONS

Moretti et al., "Molecular Cloning of a Human Vent-Like Homeobox Gene," *Genomics*, vol. 76, No. 1-3, pp. 21-29, (2001).
Reya et al., "Wnt signaling in stem cells and cancer," *Nature*, vol. 434, pp. 843-850, (2005).
Arseni et al., "The VENT-like homeobox gene ventx2 is expressed in human hematopotetic progenitor cells and promotes human myeloid development in vitro and in vivo."; Annals of Hematology, (Feb. 2008) vol. 87, No. Suppl. 1, pp. S15; Conference on Acute Leukemias XII—Biology and Treatment Strategies, Munich, Germany. Feb. 26-20.
Sedlon et al., 33$^{rd}$ Annual Meeting; ISEH—Abstracts/Experimental Hematology 2004; 32:31-104, Abstract #30.
Gao et al., Gastroenterology, (Apr. 2005) vol. 128, No. 4, Suppl. 2, p. A488. Annual Meeting of the American-Gastroenterological-Association1Digestive-Disease-Week. Chicago, IL, USA. May 14-19, 2005. Amer Gastroenterol Assoc.; abstract T1482.
Gao et al. Gastroenterology, (Apr. 2008) vol. 134, No. 4, Suppl. 1, p. Digestive Disease Week Meeting/1 09th Annual Meeting of the American-Gastroenterological-Association. San Diego, CA, USA. May 17-22, 2008. Amer Gastroenterol Assoc.; abstract W1966.
Tannock and Hill. The Basic Science of Oncology. 1998. New York: McGraw-Hill.
Song et al., Expert Opin Bioi Ther 7(4): 431-438, 2007.
van der Wouden et al., Cochrane Database Syst Rev. 2009; 7: CD004767.
Gorouhi and Maibach, International Journal of Cosmetic Science; 2009: 31: 327-345.
Kligman et al., Dermatol Surg. 1998; 24:325-8.
Rocklin et al., J.lmmunol.1981; 127: 534-539.
XP002557883 Arseni et al.; "The vent-like homeobox gene VENTX2 is a novel candidate for a human hematopoietic regulatory protein" Annals of Hematology; vol. 85, No. Suppl 1., Feb. 2006 p. 18.
XP002557884 Database EMBL Sequence 401 from Patent WO20044076622, Sep. 27, 2004.
XP002557885 Ladher et al.; Xom: a Xenopus homeobox gene that mediates the early effects of BMP-4; Development, 122(8); 2385-2394, Aug. 8, 1996.
XP002557886 Moreau-Aubry et al; A processed pseudogene codes for a new antigen recognized by a CD8<+> T cell clone on melanoma; Journal of Experimental Medicine; 191(9):1617-1623, May 1, 2000.
XP002557887 Grier et al.; The pathophysiology of HOX genes and their role in cancer; Journal of Pathology; 205(2):154-171 Jan. 2, 2005.
XP002557888 Database Geneseq Feb. 18, 2002.
XP002557889 Database Biosis "regulation of Bmp4 signaling by phosphorylation dependent proteolysis of xom"; Apr. 2005.
XP002557890 Hong et al.; "Hom-1 inhibits tumor growth in both p53 sufficient and deficient colon cancer cells"; Gastroenterology, 134(4), Suppl. 1 p. A744 Apr. 2008.
XP002557891 Arseni et al; "The vent-like homeobox gene VENTX2 is expressed in human hematopoietic progenitor cells and promotes human myeloid development in vitro and in vivo" Blood; 110(11) part 1; pp. 383A-384A, 2007.

(Continued)

*Primary Examiner* — Christina Borgeest
(74) *Attorney, Agent, or Firm* — Cesari and McKenna, LLP

(57) ABSTRACT

Disclosed are composition and methods for treating development-related disorders. Also disclosed are diagnosis methods, prognosis methods, and drug screening methods.

15 Claims, No Drawings

(56) References Cited

OTHER PUBLICATIONS

XP002557892 Arseni et al.; "VENTX2—A vent-like homeobox gene- is a novel candidate for a hematopoietic regulatory protein"; Experimental Hematology; 35(9), Suppl. 2 p. 45, Sep. 2007.

XP002557894 Hong et al.; "Xom interacts with and stimulates transcriptional activity of LEF1/TCFs: implications for ventral cell fate determination during vertebrate embryogenesis" Cell Research; 17(4):345-356, Apr. 2007.

Lee et al., JBC, 1996; 271:11897-11903.

Griffiths et al. N. Engl. J. Med. 1993; 329:530-5.

Allison, et al., "Microarray data analysis: from disarray to consolidation and consensus", Nature Reviews: Genetics. vol. 1, No. 1, 2006.

Orntoft, et al., "Genome-wide Study of Gene Copy Numbers, Transcripts, and Protein Levels in Pairs of Non-invasive and Invasive Human Transitional Cell Carcinomas", Molecular & Cellular Proteomics, vol. 1, No. 1, 2002.

Nishanian, et al., "Suppression of Tumorigenesis and Activation of Wnt Signaling by Bone Morphogenetic Protein 4 in Human Cancer Cells", Cancer Biology & Therapy, 3:7, pp. 667-675, 2004.

CANCER PROGNOSIS BY DETERMINING PHOSPHORYLATION OF A XOM POLYPEPTIDE

RELATED APPLICATION

This application is a continuation of U.S. application Ser. No. 13/206,003, filed Aug. 9, 2011, which is a divisional of U.S. patent application Ser. No. 11/677,828, filed Feb. 22, 2007, which claims priority to U.S. Provisional Application No. 60/775,645, filed Feb. 22, 2006. The prior applications are incorporated herein by reference in their entirety.

BACKGROUND

One of the fundamental questions facing development biologist is how a multi-cell organism develops from a fertilized egg, a totipotent stem cell, which contains a simple symmetrical structure, into an adult, which has a three-dimensional body plan. Dysregulation of this process results in aborted embryogenesis during early development and frequently results in tumor formation in adult life. There is a need for agents and methods for regulating the development process and treating various disorders related to dysregulated development, such as cancers, degenerative diseases, and immune disorders.

The Wnt signaling pathway is involved in the proliferation or differentiation of various stem cells. For example, it plays essential roles in the differentiation of hematopoietic stem cells derived from fetal tissue or bone marrow. Bone morphogenic proteins (BMPs) belong to the TGF-β super family and are found in species ranging from flies to mammals. The BMP signal pathway is important in cell fate determination and pattern formation during embryogenesis and in the maintenance of tissue homeostasis in the adult. The BMP pathway is also involved in regulation of morphogenesis and postnatal regeneration of GI development. See, e.g., U.S. Pat. Nos. 6,824,971, 6,159,462, 6,465,249, and 6,165,748.

SUMMARY

This invention relates to treating cancers, degenerative diseases, and immune disorders, and identifying compounds for treating these disorders using the Wnt/β-catenin or BMP4/Xom signaling pathway. Shown below are the polypeptide and nucleotide sequences of Xom and its human homologue Hom.

```
Xom polypeptide (SEQ ID NO: 7):
mtkafssvew laqssrrshr eqpskvdqry spypspslps wnsdvspssw nsqlspdpds aqvspcpasa qvspyssdse islysheeea sfygmdlnts sspgdngllh semvsvpdni prassdedaa ksayststds gyesetscss stapegdais lspndtsdee gkmgrrlrta ftsdqistle ktfqkhrylq aserqklaak lqlsevqikt wfqnrrmkyk reiqdgrpds yhpaqffgvy gyaqqptpvf qhavqhpypg ynplmetlpg tmpytmhppa mdsmtpfnsq pfqmlylpqq hlgqpltyqe
``` erpfvry
(Underlined: Ser140 and Ser144 residues,
and aa.176-233/ homeodomain/SEQ ID NO.: 3)

```
Xom cDNA nucleotide sequence
(SEQ ID NO: 10):
agaacacaag gactaataca gacaagatga ctaaagcttt ctcctctgtt gaatggcttg ctcaaagcag ccgcagatct cacagagagc agccaagcaa agtggatcag agatattcac cgtacoccag gccatccctg ccttcctgga acagtgatgt gtccccttct tcatggaaca gccaactatc tccagatcca gacagtgccc aagtctcacc atgcoctgtg agtgcacaag tatctccata ttcctcagac agtgaaatat cactgtattc acatgaagaa gaagcctctt tctatggaat ggactttaat acatcatcat cccctggaga caatggattg ctacacaggg acacaacctc atactccaga ggaatggagg ccatgtcggc cagcactcca gcaacatcac ctgtgaaagg ggcacaacct gttgattccg cctacagcac tagcactgac tcaggctatg aaagtgaaac gagtcgatcc aactctacag cccctgaagg agatgcctcc gtatctctga gtcccaatga tacctcagat gaagagggca agatgggccg aaggttgagg acggctttca ccagtgatca gatctccact ctggagaaga cttttcagaa acacagatac cttgggggcgt ctgaaagacg gaaactcgca gccaaactcc agctttctga agtccagatt aaaacttggt tccagaaccg caggatgaaa tacaaacggg aaatccaaga tggcagacca gactcatacc acccagccca gttctttggt gtgtacggct atgcacagca gcccactcct gtattccagc atgcagtcca acatccctac ccaggttata acccactaat ggaaaccctg cctggtacca tgccctatac catgcatcca cctgccatgg actctctgac tcccttcaac tctcaacctt ttcagatgct ctacctgcoc caacagcacc ttgggcaacc tctggcctat taggaagaaa ggccatttgt tagatattaa tctagaactt ataaaaggac tatactaaag gctggactt tccatggact tctgtcctcc cgcaggacaa acaaaattgc actgaatatt gttattgaca agatgtttac tgaatggatg gctaatattg ggccatgtgt tgacatgatt ttattcacat tgaatagtgg cgtgtatatt ctatgaaaaa taccatttat atgactaata aatgtaagtt atatttaaaa aaaaaaaaa a
(underlined: coding sequence
(nt27 to 1013)/SEQ ID NO: 8)
```

```
Hom polypeptide (SEQ ID NO: 5):
mrlssspprg pqqlssfgsv dwlsqsscsg pthtprpadf slgslpgpgq tsgareppqa vsikeaagss nlpapertma glskepntlr aprvrtaftm eqvrtlegvf qhhqylsple rkrlaremql sevqiktwfq nrrmkhkrqm qdpqlhspfs
```

-continued gslhappafy stssglangl qllcpwapls gpqalmlppg sfwglcqvaq ealasagasc cgqplashpp tpgrpslgpa lstgprglca mpqtgdaf
(Underlined: aa. 93-151/
homeodomain/SEQ ID NO.: 1)

Hom nucleotide sequence (SEQ ID NO: 9):
acctggccgc c<u>atgcgcctc tcctcctccc cacctcgtgg cccgcagcag ctctccagct ttggctccgt ggactggctc tcccagagca gctgctcagg gccgaccac accccaggc ctgccgactt ctccctgggg agcctcctg gcccaggcca gacatccggc gcccgggagc ccctcaggc cgtcagcatc aaggaggccg ccgggtcctc aaatctgcct gcgccggaga ggaccatggc cgggttgagt aaggagccaa ataccttgcg ggcccccgt gtccgcacag ccttcaccat ggagcaggtc cgcaccttgg agggcgtctt ccagcaccac cagtacctga gccctctgga gcggaagagg ctggccaggg agatgcagct ctcagaggtc cagataaaaa cctggtttca gaatcgccgc atgaaacaca aacggcaaat gcaggacccc cagctgcaca gccccttctc ggggtctctc catgcgcccc cagctttcta ctcaacgtct tctggccttg ccaatggcct gcagctgctg tgcccttggg caccctgtc cgggcccag gctctgatgc tgcccctgg ctccttctgg ggtctctgcc aagtggcaca agaggccctg gcatctgcgg gagcttcctg ctgcgggcag cctctggcgt cccacccccc taccccaggc cggccttcgc tgggaccagc cctgtccacg gggcccggg gcctgtgtgc tatgccacag acggggggatg catttgagg</u> aggcacctct gactcccaca ctcgcggtct tgctgatcgc acctggctcc tacctggagg actcagttgt tctgtttaca tcctggtggc acctctcacc ctgacccaca caaaggttct ggagattact ggagaatata tataaatata tatatgtacg tatatatgta aatacacata tacgtatata taaatatata tatacatatg tgtgtgtata tatatatata ttttttttttt ttttttttttt tttgagacgg agtgttgctc tgtcacccag gctggagtgc aatgacgcaa tctcggctca ctgcaacctc cgcctcctgg gttcaagcga ttctccagcc tcagcctccc gagtagctgg gattacagac acccgccacc acgcccggct aattttttct atttttagta gaaatgggt ttcaccatgt tagccaggct ggtctcaaac tcctgaccct gtgatccgcc cgcctcggcc tcccaaagtg ctgggattac aggcatgagc cactgcaccc ggccctgaga atatatttat taaagccacc tcttcactga aagttaccga aagagtcggt ttaggaagga acgaagggt cagtgaacag agtcaaatgc agaagtgggc ttgtcatggg tagggctttc ggcgtacgat aaaaggatca tttgttttt aaaaggggtt ggaaaaactg gttttccagt tggaaacagt aaaggttgta agctttgtgt gtacaaaaga aaacagggaa tgcaggtgtg tttatagcgt tgtggttcaa gtccctctta acaagaactc caaagctgga aagcaggagg gaacaaaggt gaacatgaag gcgaggatgc tggggccctg cagtgcgctc taggctgtgc gtgagccggg actgtaccca cagcttgctg agggctgctc ttcttgggcc agggaaagca gggcagccgg gacctgcggc tgtgcctgga ctgaagctgt cccgcaggtc cccaccctcc aacacgtgct cacctgtccc cctcctcgca gcagcctcgg gacaaaacaa tgactcaagg acagcacttc tcgcagaagg tctggaagtg cccagaatgg gaggcacgga agcccctccc ggggaggact cccgcgttga tggaccgttc ttggtcaga ctcctgactg cgtgcatgaa acctgagaca agtgcaattc cttccatgtc gccccagagt gcccaggagg caggcagtgc ggggtgccca ggcagacggg ttcagcctgc agaactggag gcgacctgtg aaacccaccc gggcacccca acaggaacag aagcgtggtc ctgcggctgc gtcccccagcg agtttcactt tccccttgct cgtttctccc ttgttgtaag tgtttacaac tggcatgtgc ttttaaacgt caggtaagag gggaacagct gctgtacatc gtcctggcga gtgacaatgt gacagaagcc tgggcgaggc cctcggaggg cagcagctgg acaggggcta ctgggtttgg cctggacagc actgatttgt ggatgtggat gggggcacgt tgtccgtgat aaaagtacaa gtgcccctca caaaaaaaaa aaaaaaa
(underlined: coding sequence
(nt12 to 788)/SEQ ID NO: 6)

In one aspect, the invention features a method for treating a cellular proliferative disorder in a subject. A cellular proliferative disorder refers to a disorder characterized by uncontrolled, autonomous cell growth, including malignant and non-malignant growth. The method includes administering to a subject in need thereof an effective amount of a polypeptide containing SEQ ID NO: 1 or 3, or a functional equivalent thereof. A "functional equivalent" refers to a polypeptide derivative of a common polypeptide, e.g., a protein having one or more point mutations, insertions, deletions, truncations, a fusion protein, or a combination thereof, and retaining substantially the ability of the common polypeptide, such as binding to a LEF1/TCF. In one example, the polypeptide lacks an LEF1/TCF transactivation domain. The cellular proliferative disorder can be a condition characterized by aberrant activation of LEF1/TCF-mediated transcription. An aberrant activation of LEF1/TCF-mediated transcription refers to a cellular condition where the LEF1/TCF-mediated transcription is abnormally high, as determined by the TOP-flash assay described in Example 1 below or any analogous assays.

The invention also features a method for treating an inflammation-related disorder in a subject. An inflammation-related disorder is characterized by a local or systemic, acute or chronic inflammation. The method includes administering to a subject in need thereof an effective amount of an inhibitor of a polypeptide containing SEQ ID NO: 1 or 3 (e.g., Xom or Hom) or a functional equivalent thereof. The inflammation-related disorder is an auto-immune disorder or an inflammatory disorder. An inhibitor of a polypeptide containing SEQ ID NO: 1 or 3 refers to a compound that reduces the protein level in a cell in a statistically significant manner. Examples of the inhibitor include an antibody, an antisense nucleic acid, and an RNAi agent, as well as small molecule compounds and naturally occurring compounds, which target Hom/Xom.

The invention also features a method for treating a degenerative disorder in a subject. A degenerative disorder is characterized by a local or systemic, acute or chronic degeneration, loss of cellular volume or cellular function. The method includes administering to a subject in need thereof an effective amount of an inhibitor of a polypeptide containing SEQ ID NO: 1 or 3 (e.g., Xom or Hom) or a functional equivalent thereof.

The invention further features a method for treating myelodysplastic syndromes. The method includes administering to a subject in need thereof an effective amount of an inhibitor of a polypeptide containing SEQ ID NO: 1 or 3, or a functional equivalent thereof.

In another aspect, the invention features a screening method of identifying a compound for treating a cellular proliferative disorder. The method includes contacting a test compound with a polypeptide containing a fragment of SEQ ID NO: 3 that include Ser 140 or Ser 144; and determining the phosphorylation of Ser 140 or Ser 144 (e.g., by a Ser140 and Ser144 phospho-specific antibody). The phosphorylation level in the presence of the compound, if lower than that in the absence of the compound, indicates that the compound is a candidate for treating the disorder. The screening method can also be conducted by contacting a test compound with a cell having a polypeptide containing a fragment of SEQ ID NO: 3 that includes Ser 140 or Ser 144; and determining the phosphorylation of Ser 140 or Ser 144. The phosphorylation level in the presence of the compound, if lower than that in the absence of the compound, indicates that the compound is a candidate for treating the disorder. The fragment is at least 14 (e.g., 15, 18, 20, 30, 50, 100, 150, 200, 250, and 300) amino acid residues in length.

The above method can also be used to identify compounds that increase the phosphorylation of Ser 140 or Ser 144. Compounds thus-identified represent candidates for treating for treating cellular degenerative disorders or inflammation-related disorders. Specifically, if the phosphorylation is higher than control, it indicates that the compound is a candidate for treating cellular degenerative disorder.

In yet another aspect, the invention features a composition that contains a polypeptide having the sequence of SEQ ID NO: 1 or 3, or a functional equivalent thereof, or an activator of the polypeptide. An activator of the polypeptide is a compound that increases the protein level of the polypeptide by either inducing its expression or repressing its proteolysis. Examples of the activator include retinoic acid, resveratrol, ellagic acid, aspirin, and their derivatives. The composition can further include salicylic acid, emodin, flavonoid, or their derivatives. In one embodiment, the composition is a topical composition, which can be used for skincare. Specifically, one can administer to a subject in need thereof a safe and effective amount of the composition. In another embodiment, the composition is a dietary composition, such as a tea, soft drink, juice, milk, coffee, jelly, ice cream, yogurt, cookie, cereal, chocolate, snack bar, candy, chewing gum, syrup, or food capsule. This dietary composition can be used to treat or slow down the onset of a cellular proliferative disorder.

In a further aspect the invention features a method of assessing a subject's cancer prognosis. The method includes obtaining a biological sample from the subject; and determining the presence of a gene encoding a polypeptide containing SEQ ID NO: 1 in the sample. The subject is determined to have a good prognosis if the gene is present on both chromosomes or to have a bad prognosis if the gene missing from one or both of the chromosomes.

One can also assess a subject's cancer prognosis by obtaining a biological sample from the subject; and determining the expression level of a gene encoding a polypeptide containing SEQ ID NO: 1 in the sample. The subject is determined to have a good prognosis if the expression level is above a control level or to have a bad prognosis if the expression level is below the control level. The control level can be obtained from a normal subject. The method can further comprise contacting the sample with a chemotherapeutical agent prior to determining the express level of a gene encoding a polypeptide containing SEQ ID NO: 1 in the sample. The biological sample can be a tumor biopsy sample or a blood sample.

Also featured is a method for diagnosing of myelodysplastic syndromes. The method includes obtaining a biological sample from the subject; and determining the expression level of a gene encoding a polypeptide containing SEQ ID NO: 1, e.g., Hom, in the sample. An abnormal increased expression level indicates the subject has or is prone to develop myelodysplastic syndromes.

Within the scope of this invention is a method for determining whether a subject has or is prone to develop systemic lupus erythematosus (SLE). The method includes obtaining a biological sample from the subject; and determining the expression level of a gene encoding a polypeptide containing SEQ ID NO: 1 in the sample. The subject is determined to have or be prone to develop SLE syndromes if the expression level is above a control level.

Within the scope of this invention is a method for maintaining a pluripotent cell, the method comprises contacting the cell with an activator of a polypeptide containing SEQ ID NO: 1. The pluripotent cell can be a stem cell, such as a hematopoietic stem cell, a gastrointestinal stem cell, a neuronal stem cell, and a skin stem cell.

Also within the scope of this invention are isolated mutant polypeptides of Xom or Hom that include the sequence of SEQ ID NO: 1 or 3. Examples of such mutant polypeptides include: XomND55, Xom ND175, XomCD145, and XomCD85, which corresponds to aa. 56-326, aa. 176-326, aa. 1-181, and aa. 1-241 of SEQ ID NO: 7 (SEQ ID NOs: 11-14, respectively). Other examples include the fusion of aa 1-130 and aa 241-326 of SEQ ID NO: 7 (SEQ ID NO: 15) and the fusion of Xom aa1-175 and plus Hom aa 93-258 (SEQ ID NO: 16). Other examples include a polypeptide containing a fragment of SEQ ID NO: 7 that includes Ser 140 or Ser 144, such as TDSGYESETSC (SEQ ID NO: 17) and its mutants in which Ser 140 or Ser 144 is substituted by other amino acid residues such as alanine. These polypeptides are least 11 (e.g., 11, 13, 15, 20, 50, 100, 150, 200, 250, and 300) amino acid residues in length. They can be used to screening inhibitors of Ser 140 or Ser 144 phosphrylation or as therapeutic agents to inhibit Ser 140 or Ser 144 phosphrylation of endogenous Xom. Within the scope of this invention are fusion proteins containing one or more of the afore-mentioned mutant sequences and a heterologous sequence. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An isolated polypeptide refers to a polypeptide free from naturally associated molecules, i.e., it is at least 75% (i.e., any number between 75% and 100%, inclusive) pure by dry weight. Purity can be measured by any appropriate standard method, for example, by column chromatography, polyacrylamide gel electrophoresis, or HPLC analysis. An isolated polypeptide of the invention can be purified from a natural source, produced by recombinant DNA techniques.

The invention also features an isolated nucleic acid that contains a sequence encoding the just-mentioned mutant or fusion polypeptide or a complement of the sequence. A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptides of this invention. For this purpose, one can operatively link the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. A vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention. Also within the scope of this invention is a host cell that contains the above-described nucleic acid. Examples include E. coli cells, insect cells (e.g., using baculovirus expression vectors), yeast cells, or mammalian cells. See e.g., Goeddel, (1990) Gene Expression Technology: Methods in Enzymology 185, Academic Press, San Diego, Calif.

To produce a mutant or fusion polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, for example, using T7 promoter regulatory sequences and T7 polymerase.

The details of one or more embodiments of the invention are set forth in the description below. Other features, objects, and advantages of the invention will be apparent from the description and from the claims.

DETAILED DESCRIPTION

This invention is based, at least in part, on the unexpected discoveries of a signal transduction component that functions as a point of convergence to mediate the combined signaling of the Wnt/β-catenin and BMP4/Xom pathways.

Xom (also known as Vent2, Vox, and Xbr-1), is a cell fate determination factor of the Vent family of Homeobox genes. It is both a transcriptional repressor and an activator (Ladher et al. 1996, Development 122, 2385-2394; Onichtchouk et al., 1996, Development 122, 3045-3053; Schmidt et al., 1996, Development 122, 1711-1721; and Papalopulu et al., 1996, Dev Biol 174, 104-114). During early embryogenesis, Xom is implicated in the formation of ventral mesoderm and in defining the dorsoventral patterning (Onichtchouk et al., 1998, Development 125, 1447-1456 and Koide et al., 2005. Proc Natl Acad Sci USA 102, 4943-4948). Zygotic Xom transcription starts after midblastula transition (MBT) and distributes from a more ubiquitous expression pattern during the early gastrula stage to the ventral-lateral regions as gastrulation proceeds (Ladher et al. 1996, Development 122, 2385-2394 and Schmidt et al., 1996, Development 122, 1711-1721). The expression of Xom appears to be positively regulated by signals from the ventral signal center, such as the BMP4, but negatively regulated by dorsal-specific genes, such as the Gooscoid (Gsc) and the noggin (Ladher et al. 1996, Development 122, 2385-2394; Onichtchouk et al., 1996, Development 122, 3045-3053). Xom expression in turn contributes to the formation of the dorsoventral pattern by promoting the expression of ventral genes such as the BMP4 and the Vent genes and inhibiting the expression of dorsal-organizer genes such as the Gsc and chordin (Onichtchouk et al., 1996, Development 122, 3045-3053; and Schmidt et al., 1996, Development 122, 1711-1721). To exert its transcriptional repressor function, Xom binds directly to the distal element of the dorsal specific gene promoters, such as the Gsc, and inhibit their transcription (Trindade et al., 1999, Dev Biol 216, 442-456).

As described herein, Xom interacts functionally with the LEF1/TCFs transcription factors. The LEF1/TCFs are a family of high mobility group (HMG) transcriptional factors that possess no intrinsic transcriptional activities. Rather, the LEF1/TCF-mediated transcription activities are tightly controlled by their associated factors (Hurlstone et al., 2002, Embo J 21, 2303-2311). In a non-induction state, the LEF1/TCFs are associated with transcriptional repressors, such as the Grouch, and CtBP, which maintain the LEF1/TCF-mediated transcription in a repressed state (Roose et al., 1998, Nature 395, 608-612; Brantjes et al., 2001, Nucleic Acids Res 29, 1410-1419; Cavallo et al., 1998, Nature 395, 604-608; Waltzer et al., 1998, Nature 395, 521-525; and Brannon et al., 1999, Development 126, 3159-3170). During early embryogenesis, local enrichment of β-catenin in the future dorsal side of embryos allows it to interact with LEF1/TCFs and to induce the expression of dorsal-specific genes, such as Siamois, Twin, and Xnr (Harland et al., 1997, Annu Rev Cell Dev Biol 13, 611-667; Brannon et al., 1997, Genes Dev 11, 2359-

2370; Laurent et al., 1997, Development 124, 4905-4916; and McKendry et al., 1997, Dev Biol 192, 420-431. Besides determination of cell fate during early embryogenesis, excessive activation of LEF1/TCF-mediated transcription of β-catenin has also been implicated as the initial step of malignant transformation of a variety of cancers (Barker et al., 2000, Adv Cancer Res 77, 1-24). The LEF1/TCF-factors are the transcriptional mediators of Wnt/β-catenin, therefore, the LEF1/TCF promoter-luciferase reporter activity has generally been regarded as an indicator of Wnt/β-catenin activities.

The role of LEF1/TCFs in ventral cell fate determination is less clear, although several studies indicate their potential involvement in the process. For example, expression profiling showed that members of LEF1/TCF family are broadly distributed in ventral-posterior regions (Molenaar et al., 1998, Mech Dev 75, 151-154 and Oosterwegel et al., 1993, Development 118, 439-448). Mutagenesis studies revealed that LEF1-/- TCF1-/- mice carry caudal defects with neural expansion (Galceran et al., 1999, Genes Dev 13, 709-717) and that loss of function of LEF1 leads to ventral rather than dorsal defects in Xenopus (Roel et al., 2002, Curr Biol 12, 1941-1945). Consistent with the possible involvement of LEF1/TCFs in ventral cell fate determination, promoter analysis revealed that many ventral genes, such as Xom and Bambi, contain LEFT/TCF binding sites. Mutations of the LEF1/TCF binding site of these ventral genes cause significant inhibition of their responsiveness to the BMP4 signaling (Karaulanov et al., 2004, Embo J 23, 844-856).

As described herein, it was found that Xom and LEF1/TCF-factors functionally interact with each other. This interaction plays an essential role in stem cell pool maintenance and cell fate determination during early embryogenesis and serves as a point of convergence to mediate the combined signaling effect of BMP/Xom and Wnt/β-catenin pathways during early embryogenesis. A human homologue of Xom, Hom, was cloned. It was found to function in a manner similar to that of Xenopus Xom. In particular, it was found that over expression of Xom/Hom in cancer cells or terminal differentiated cells results in cell growth arrest or cell death.

Also, when combined together, expression of the LEF1/TCF factors and Xom or forced expression of Hom induces cell death in colon cancer cells, with the efficacy of near 100%. Similar effects were found in cervical cancer cells and prostate cancer cells. Further, it was found that a number of cancer chemotherapy drugs or treatment, e.g., 5-FU, DOX, and radiations, induced the expression of Xom or Hom. These discoveries suggest that Xom/Hom behaves like a tumor suppressor and can be used in cancer diagnosis, prognosis, and treatment. The fact that the gene encoding Hom is located at 10q26, which is prone to loss during oncogenesis and cancer metastasis, supports the roles of Hom/Xom in cancer diagnosis, prognosis, and treatment.

Hom/Xom's stability is critical for stem cell pool maintenance and cell-fate determination. The protein level of Xom is controlled by proteolysis, which in turn is controlled by phosphorylation of Ser140/144. During development, endogenous Xom was rapidly degraded at the onset of gastrulation. Xom Ser140/144 was not phosphorylated during the pre-gastrulation period but become rapidly phosphorylated at the onset of gastrulation, a pattern in reciprocal relationship to the Xom stability. It was also found that the phospho-moiety plays a critical role in mediating the binding between Xom and β-TRCP (the E3 ligase that mediates Xom protreolysis) and that non-phosphorylatable Xom mutant is resistant to proteolysis. Furthermore, while expression of wild-type Xom alone causes growth arrest in 30% colon cancer cells, expression of stable Xom mutant causes growth arrest in 60% colon cancer cells. This phosphorylation and proteolysis processes represent novel therapeutic targets for identifying new drugs for treating cancer and other disorders.

Besides the stability, the expression of Hom/Xom is also crucial of various development processes. For example, it was found that Hom production can be induced by GM-CSF and IL4 in the CD14+ blood progenitor cells. This induction leads to terminal differentiation of the CD14+ cells (which are a monocyte progenitor cell) into dendritic cells to present antigen and thereafter undergo apoptosis.

Dendritic cells are immune cells and form part of the mammalian immune system. Their main function is to process antigen material and present it on their surface to other cells of the immune system. Dendritic cells are present in small quantities in tissues that are in contact with the external environment, mainly the skin (where they are often called Langerhans cells) and the inner lining of the nose, lungs, stomach and intestines. They can also be found at an immature state in the blood. Once activated, they migrate to the lymphoid tissues where they interact with T cells and B cells to initiate and shape the immune response. Altered function of dendritic cells plays a major or key role in allergy and autoimmune diseases like lupus erythematosus. Allergy is a pathologically overblown reaction to an outside allergen; autoimmune diseases are erroneous immune reactions to the organism's own antigen. See, e.g., Santiago-Schwarz et al. J Immunol. 2001 Aug. 1; 167(3):1758-68. Given the roles of dendritic cells, modulating expression of Xom/Hom in dendritic cells presents a way to treat autoimmune disease and inflammation. For example, Xom/Hom modulates the differentiation of dendritic cells in at least two stages, i.e., (i) an earlier stage when CD14+ blood progenitor cells, in response to GM-CSF and IL4, terminally differentiate into dendritic cells and (ii) a terminal stage when terminally differentiated dendritic cells have already formed as, e.g., Langerhans cells in the skin. At the earlier stage, Xom/Hom expression or activity is required for CD 14+ blood progenitor cells differentiation into progenitor of dendritic cells. Accordingly, blocking Xom/Hom expression or activity can lead to fewer dendritic cells, thereby reducing unwanted immune response. At the terminal stage, on the other hand, high level of Xom/Hom expression or activity forces the terminally differentiated dendritic cells into apoptosis. It follows, at this stage, high level of Xom/Hom expression or activity depletes, via inducing apoptosis, the terminally differentiated dendritic cells, thereby also reducing unwanted immune response, in particular, that in the skin.

Diagnostic and Prognostic Assays

A cancer cell or a cell prone to tumorigenesis can be detected in a subject based on the absence of the Hom polypeptide (e.g., antibody) or a nucleic acid (e.g., genomic DNA or mRNA) encoding the polypeptide in a test sample from the subject. In other words, the polypeptide and nucleic acids can be used as markers to indicate the presence or absence of a cancer cell. Diagnostic and prognostic assays of the invention include methods for assessing the expression level of the Hom polypeptide or nucleic acid and for identifying variations and mutations in the sequence of the Hom polypeptide or nucleic acid.

The presence, level, or absence of the Hom polypeptide or nucleic acid in a test sample can be evaluated by obtaining a test sample from a test subject and contacting the test sample with a compound or an agent capable of detecting the Hom polypeptide or nucleic acid (e.g., mRNA or genomic DNA probe). The "test sample" includes tissues, cells and biological fluids isolated from a subject, as well as tissues, cells and fluids present within a subject. The level of expression of the Hom gene can be measured in a number of ways, including measuring the mRNA encoded by the Hom gene; measuring the amount of polypeptide encoded by the Hom gene; or measuring the activity of polypeptide encoded by the Hom gene.

The level of mRNA corresponding to the Hom gene in a cell can be determined both by in situ and by in vitro formats. Messenger RNA isolated from a test sample can be used in hybridization or amplification assays that include, Southern or Northern analyses, PCR analyses, and probe arrays. One preferred diagnostic method for the detection of mRNA levels involves contacting the isolated mRNA with a nucleic acid probe that can hybridize to the mRNA encoded by the Hom gene. The probe can be a full-length Hom nucleic acid, such as the nucleic acid of SEQ ID NO: 6 or a portion thereof, such as an oligonucleotide of at least 10 nucleotides in length and sufficient to specifically hybridize under stringent conditions to Hom mRNA or genomic DNA.

In one format, mRNA (or cDNA prepared from it) is immobilized on a surface and contacted with the probes, for example, by running the isolated mRNA on an agarose gel and transferring the mRNA from the gel to a membrane, such as nitrocellulose. In another format, the probes are immobilized on a surface and the mRNA (or cDNA) is contacted with the probes, for example, in a gene chip array. A skilled artisan can adapt known mRNA detection methods for use in detecting the level of mRNA encoded by the Hom gene.

The level of mRNA (or cDNA prepared from it) in a sample encoded by Hom gene can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115: 379-402, 1999), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule comprising the nucleotide sequence flanked by the primers.

For in situ methods, a cell or tissue sample can be prepared and immobilized on a support, such as a glass slide, and then contacted with a probe that can hybridize to genomic DNA on chromosomes or mRNA that encodes the Hom polypeptide.

In another embodiment, the methods of the invention further include contacting a control sample with a compound or agent capable of detecting Hom mRNA, or genomic DNA, and comparing the presence of Hom mRNA or genomic DNA in the control sample with the presence of Hom mRNA or genomic DNA in the test sample.

The above-described nucleic acid-based diagnostic methods can provide qualitative and quantitative information to determine whether a subject has or is predisposed to a disease associated with aberrant Hom gene expression, e.g., cancers.

A variety of methods can be used to determine the level of Hom polypeptide. In general, these methods include contacting an agent that selectively binds to the polypeptide, such as an antibody, to evaluate the level of polypeptide in a sample. Antibodies can be polyclonal, or more preferably, monoclonal. An intact antibody, or a fragment thereof (e.g., Fab or F(ab')$_2$) can also be used. In a preferred embodiment, the antibody bears a detectable label. The term "labeled", with regard to the probe or antibody, is intended to encompass direct labeling of the probe or antibody by physically linking a detectable substance to the probe or antibody, as well as indirect labeling of the probe or antibody by reactivity with a detectable substance. For example, an antibody with a rabbit Fc region can be indirectly labeled using a second antibody directed against the rabbit Fc region, wherein the second antibody is coupled to a detectable substance. Examples of detectable substances are provided herein. Appropriate detectable substance or labels include radio isotopes (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.).

The detection methods can be used to detect the Hom polypeptide in a biological sample in vitro as well as in vivo. In vitro techniques for detection of the Hom polypeptide include ELISAs, immunoprecipitations, immunofluorescence, EIA, RIA, and Western blotting analysis. In vivo techniques for detection of the Hom polypeptide include introducing into a subject a labeled anti-Hom antibody. For example, the antibody can be labeled with a detectable substance as described above. The presence and location of the detectable substance in a subject can be detected by standard imaging techniques.

Xom Ser140/144 phosphorylation levels can also be used as an indicator of tumorigenicity. More specifically, higher ser140/144 phosphorylation than control (or kinase activity) indicates a higher likelihood of developing tumor/cancer. Ser140/144 phosphorylation can be measured using the Xom related sequence and Ser140/144 phospho-specific antibody or mass spectrometry (Liu et al., Cell 108 P837-47 and Gerber et al., PNAS 100, P6940-5).

The diagnostic methods described herein can identify subjects having, or at risk of developing, a disease or disorder associated with aberrant Hom expression or activity.

The prognostic assays described herein can be used to determine whether a subject is suitable to be administered with an agent (e.g., an agonist, antagonist, peptidomimetic, protein, peptide, nucleic acid, small molecule, or other drug candidate) to treat a cancer. For example, such assays can be used to determine whether a subject can be administered with a cytotoxic drug to treat a cell proliferation disorder.

Also featured is a method of monitoring a treatment for a cancer in a subject. For this purpose, gene expression levels of Hom can be determined for test samples from a subject before, during, or after undergoing a treatment. An increase of the expression level of Hom after the treatment indicates that the subject can be further treated by the same treatment. Ser140/144 phosphorylation of an exogenous Xom peptide can also be used as a monitor of cancers, degenerative diseases and inflammatory/autoimmune diseases activities. For example, one can use a Xom protein or its fragment containing the Ser140/144 phosphrylation site as a substrate, take cells from a subject, and make a cellular extract. Then, the Xom polypeptide is incubated with the extract and monitoring Ser140/144 phosphorylation with Ser140/144 phospho specific antibody. Alternatively, one can express a Xom polypeptide or its fragment having Ser140/144 in a cell obtained from a subject and determine the Ser140/144 phosphorylation level. The level reflects a stage of the disorder based on the teaching provided herein and that known in the art.

Information obtained from practice of the above diagnostic assays is useful in prognostication, identifying progression of, and clinical management of diseases and other deleterious conditions affecting an individual's health status. In preferred embodiments, the foregoing diagnostic assays provide information useful in prognostication, identifying progression of and management of malignancies (cancers) that are characterized by lack or abnormal low level Hom expression. The information more specifically assists the clinician in designing chemotherapeutic or other treatment regimes to eradicate such malignancies from the body of an afflicted mammal, typically a human.

Drug Screening

The invention features a method for identifying a compound that enhances the activity of Hom/Xom by inducing its expression or promote its stability via, e.g., inhibiting phosphorylation of Ser140/144. The compound thus-identified can be used to treat cancer, degenerative disorders, or immune disorders.

A compound that reduces Xom/Hom protein phosphorylation level in a statistically significant manner (i.e., Xom/Hom kinase inhibitor) can be identified according to the methods described below.

Candidate compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

To identify a Xom/Hom activator or a Xom/Hom kinase inhibitor, one can contact a candidate compound with a system containing a Xom/Hom gene or polypeptide. The system can be a cell-free system or a cell-containing system, e.g., an in vitro cell line model or an in vivo animal model. In a cell-containing system, cells can naturally express the Xom/Hom gene, or can be modified to express a recombinant nucleic acid. The recombinant nucleic acid can contain the Xom/Hom gene coding region fused to a heterologous promoter or a Xom/Hom gene promoter sequence fused to a reporter gene. One then measures the expression level or the phosphorylation level of the Xom/Hom polypeptide (e.g., that at Ser 140 or Ser 144). A Xom/Hom polypeptide described above can be a full-length Xom/Hom polypeptide or its fragment that contains the phosphorylation sites.

The expression level can be determined at either the mRNA level or at the protein level. Methods of measuring mRNA levels in a cell, a tissue sample, or a body fluid are well known in the art. To measure mRNA levels, cells can be lysed and the levels of mRNA in the lysates or in RNA purified or semi-purified from the lysates can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out using tissue sections or unlysed cell suspensions, and detectably (e.g., fluorescent or enzyme) labeled DNA or RNA probes. Additional mRNA-quantifying methods include RNA protection assay (RPA) and SAGE. Methods of measuring protein levels in a cell or a tissue sample are also known in the art.

Methods of measuring the phosphorylation level of a polypeptide are also known in the art. Examples of the methods include using specific phospho-antibodies or mass spectrometry (Liu et al., Cell 108 P837-47 and Gerber et al., PNAS 100, P6940-5).

To determine the ability of a candidate compound to increase Xom/Hom expression level or inhibit its phosphorylation level, one compares the level obtained in the manner described above with a control level or activity obtained in the absence of the candidate compound. If the phosphorylation level is lower than the control, or if the expression level is higher than the control, the compound is identified as being effective for treating the disorders mentioned above. One can further verify the efficacy of a compound thus-identified using a Xenopus occyte model or an animal model. One can administer the compound to Xenopus oocyte model or an animal models and exam them according to the method describe below in the Example section or other standard techniques. Any statistically significant increase in cell death indicates the compound is a candidate for treating the disorders mentioned above.

Inhibitors of Xom/Hom can also be identified using the above-described methods except that a candidate compound is identified if it repress the expression of Xom/Hom or increase the phosphorylation level.

Treatment Methods

The invention also features methods for treating in a subject a cellular proliferative disorder (e.g., cancer), a cellular degenerative disorder, an inflammation-related disorder (eczema and inflammatory bowel diseases), or a hematological condition (e.g., myelodysplastic syndromes).

A cellular proliferative disorder refers to a disorder characterized by uncontrolled, autonomous cell growth, including malignant and non-malignant growth. Examples of this disorder include colon cancer, breast cancer, prostate cancer, hepatocellular carcinoma, melanoma, lung cancer, glioblastoma, brain tumor, hematopoeitic malignancies, retinoblastoma, renal cell carcinoma, head and neck cancer, cervical cancer, pancreatic cancer, esophageal cancer, and squama cell carcinoma.

An inflammation-related disorder is characterized by a local or systemic, acute or chronic inflammation. Examples include inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), acute respiratory distress syndrome, fulminant hepatitis, hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), asthma, and allergic rhinitis. Examples also include autoimmune diseases (e.g., rheumatoid arthritis, psoriatic arthritis, systemic lupus erythematosus, myasthenia gravis, juvenile onset diabetes, glomerulonephritis, autoimmune throiditis, ankylosing spondylitis, systemic sclerosis, and multiple sclerosis), acute and chronic inflammatory diseases (e.g., systemic anaphylaxia or hypersensitivity responses, drug allergies, insect sting allergies, allograft rejection, and graft-versus-host disease), Sjogren's syndrome, human immunodeficiency virus infection, cancer (e.g., brain, breast, prostate, colon, kidney, ovary, thyroid, lung, and hematopoietic cancer), and tumor metastasis.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

A subject to be treated for a cellular proliferative disorder can be identified by standard diagnosing techniques for the disorder. Optionally, the subject can then be examined for the gene expression or activity level of the Xom/Hom gene or polypeptide by methods described above. If the gene expression or activity level is lower in a sample from the subject than that in a sample from a normal person, the subject is a candidate for treatment with an effective amount of a Xom/Hom peptide or activator. A subject to be treated for an inflammation-related disorder can be identified by standard diagnosing techniques.

"Treating" refers to administration of a compound to a subject, who has a cellular proliferative disorder (e.g., cancer), an inflammation-related, or a hematological condition, with the purpose to cure, alleviate, relieve, remedy, prevent, or ameliorate the disorder, the symptom of the disorder, the disease state secondary to the disorder, or the predisposition toward the disorder. An "effective amount" refers to an amount of the compound that is capable of producing a medically desirable result, e.g., as described above, in a treated subject. The treatment method can be performed in vivo or ex vivo, alone or in conjunction with other drugs or therapy.

In an in vivo approach, a compound is administered to a subject. Generally, the compound is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Examples of compounds that can be used to treat a cellular proliferative disorder or an inflammation-related disorder include polypeptides that have SEQ ID NO: 1 or 3 and lack the LEF1/TCF transactivation domain. The examples also include functional equivalents of SEQ ID NO: 1 or 3. As described above, a functional equivalent of SEQ ID NO: 1 or 3 refers to a polypeptide derived from the SEQ ID NO: 1 or 3, e.g., a fusion polypeptide or a polypeptide having one or more point mutations, insertions, deletions, truncations, or combination thereof. This polypeptide is at least 60% (any number between 60% and 100%, inclusive) identical to SEQ ID NO: 1 or 3 and retains substantially activity of the homeodomain activity of Xom or Hom, i.e., the ability to bind to LEF1/TCF and inhibit LEF1/TCF-dependent transcription in a dominant negative manner by competing for endogenous LEF1/TCF activator, such as β-catenin. LEF1/TCF factors are essential high mobility group (HMG) containing transcriptional factors. The LEF1/TCFs contains little transcriptional activity by themselves, rather LEF1/TCFs are activated by associated factors, such as the β-catenin of the Wnt pathway and Xom of the BMP4 pathway. Transactivation of LEF1/TCFs by the β-catenin or Xom has been found to be essential for stem cells function and cell fate determination as well as malignant transformation.

The aforementioned polypeptides can be synthesized using methods known in the art or be prepared using recombinant technology. For example, one can clone a nucleic acid encoding the polypeptide in an expression vector, in which the nucleic acid is operably linked to a regulatory sequence suitable for expressing the polypeptide in a host cell. One can then introduce the vector into a suitable host cell to express the polypeptide. The expressed recombinant polypeptide can be purified from the host cell by methods such as ammonium sulfate precipitation and fractionation column chromatography. See Goeddel, (1990) Gene Expression Technology: Methods in Enzymology 185, Academic Press, San Diego, Calif. A polypeptide thus prepared can be tested for its activity according to the method described in the examples below.

Examples of compounds that can be used to treat cellular proliferative disorders include those that increase the protein level of Hom, such as 5-FU, DOX, radiation, retinoic acid, GM-CSF-IL4), resveratrol, ellagic acid, aspirin, salicylic acid, emodin and flavonoid and their derivatives that induce Hom expression. Also can be used are those that inhibit Xom/Hom's phosphorylation (i.e., Xom/Hom kinase inhibitors), such as resveratrol, ellagic acid, aspirin, salicylic acid, emodin and flavonoid and their derivatives.

Compounds that inhibit the expression or activity of Hom/Xom can also be use to treat other disorders, such as Myelodysplastic syndromes (MDS). MDS, also known as "preleukemia," are a diverse collection of hematological conditions united by ineffective production of blood cells and varying risks of transformation to acute myelogenous leukemia. Although not a true malignant neoplasm, MDS is nevertheless classified within the hematological neoplasms. It was found that Hom was over-expressed in an MDS patient, suggesting the blockage of the differentiation progress by Hom. Thus, an inhibitor of Hom/Xom can be used to treat MDS. Examples of the inhibitor include an antibody, an antisense nucleic acid, and an RNAi agent that specifically target Hom/Xom. Other examples include compounds that inhibit the expression of Hom.

An "antibody" includes intact molecules as well as fragments thereof, such as Fab, F(ab')2, Fv, scFv (single chain antibody), and dAb (domain antibody; Ward, et al. (1989) Nature, 341, 544). A derivative of an antibody refers to a protein or a protein complex having a polypeptide variant of this invention. An antibody or derivative of this invention can be made by co-expressing corresponding light and heavy chain CDRs-containing polypeptides in a suitable host cell by methods known in the art. See, e.g., Harlow and Lane, (1988) Antibodies: A Laboratory Manual, Cold Spring Harbor Laboratory, New York.

To make an antibody described herein, the Xom or Hom polypeptide or its antigenic fragment can be coupled to a carrier protein, such as KLH, mixed with an adjuvant, and injected into a host animal. Antibodies produced in that animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies, heterogeneous populations of antibody molecules, are present in the sera of the immunized subjects. Monoclonal antibodies, homogeneous populations of antibodies to a particular antigen, can be prepared using standard hybridoma technology. See, e.g., Kohler et al. (1975) Nature 256, 495; Kohler et al. (1976) Eur. J. Immunol. 6, 511; Kohler et al. (1976) Eur. J. Immunol. 6, 292; and Hammerling et al. (1981) Monoclonal Antibodies and T Cell Hybridomas, Elsevier, N.Y. In particular, monoclonal antibodies can be obtained by any technique that provides for the production of antibody molecules by continuous cell lines in culture such as described in U.S. Pat. No. 4,376,110; the human B-cell hybridoma technique (Kosbor et al. (1983) Immunol Today 4, 72; Cole et al. (1983) Proc. Natl. Acad. Sci. USA 80, 2026) and the EBV hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

A polynucleotide containing a nucleic acid sequence encoding an inhibitor of Xom or Hom can be used to treat an inflammation-related disorder. The nucleic acid sequence can encode the above-described polypeptide, an anti-Xom or Hom antibody, an anti-sense RNA, or a small interference RNA (e.g., an RNAi agent) that targets the Xom or Hom and inhibits its expression activity.

The term "RNAi" or "RNA interference" refers to a sequence-specific or selective process by which a target molecule (e.g., a target gene, protein or RNA) is down-regulated. Within the scope of this invention is utilization of RNAi featuring degradation of RNA molecules (e.g., within a cell). Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free double-stranded RNA, which directs the degradative mechanism. Alternatively, RNAi can be initiated by the hand of man, for example, to silence the expression of target genes.

The term "RNAi agent" refers to an RNA (or analog thereof), having sufficient sequence complementarity to a target RNA (i.e., the RNA being degraded) to direct RNAi. A RNA agent having a "sequence sufficiently complementary to a target RNA sequence to direct RNAi" means that the RNA agent has a sequence sufficient to trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent can also have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence. The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double-stranded, i.e., dsRNA and dsDNA, respectively).

The polynucleotide can be delivered by the use of polymeric, biodegradable microparticle or microcapsule delivery devices known in the art. Another way to achieve uptake of the nucleic acid is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

In the above-mentioned polynucleotides, e.g., expression vectors, the nucleic acid sequence encoding an inhibitor of Xom or Hom is operatively linked to a promoter or enhancer-promoter combination. Suitable expression vectors include plasmids and viral vectors such as herpes viruses, retroviruses, vaccinia viruses, attenuated vaccinia viruses, canary pox viruses, adenoviruses and adeno-associated viruses.

As is well known in the art, the dosage for a patient depends upon various factors as described above. Dosages will vary, but a preferred dosage for administration of polynucleotide is about $10^6$ to $10^{12}$ copies of the polynucleotide molecule. This dose can be repeatedly administered as needed. Routes of administration can be any of those listed above.

Also within the scope of the invention is a packaged product including a container, an effective amount of one of the above-described compound and a legend associated with the container and indicating administration of the compound for treating a subject suffering from or being at risk for developing the disorder mentioned above. The compound can be admixed with a pharmaceutically acceptable carrier, including a solvent, a dispersion medium, a coating, an antibacterial and antifungal agent, and an isotonic and absorption-delaying agent.

The compound can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the compound with a solid carrier and a lubricant. Examples of solid carriers include starch and sugar bentonite. The compound can also be administered in a form of a hard shell tablet or a capsule containing a binder, e.g., lactose or mannitol, a conventional filler, and a tableting agent. The compound can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The efficacy of the compound can be evaluated both in vitro and in vivo. For example, the compound can be tested for its ability to arrest cell growth or induce apoptosis in vitro. For in vivo studies, the compound can be injected into an animal (e.g., an animal model) and its effects on cell growth or apoptosis are then accessed. Based on the results, an appropriate dosage range and administration route can be determined.

Stem Cells

A stem cell is a cell that is capable of differentiating into a number of final, differentiated cell types. Stem cells may be totipotent, pluripotent, mulitpotent, or unipotent. Totipotent stem cells are produced from the fusion of an egg and sperm cell. Cells produced by the first few divisions of the fertilized egg are also totipotent. These cells can differentiate into embryonic and extraembryonic cell types. Totipotent stem cells typically have the capacity to develop into any cell type. Totipotent stem cells are usually embryonic in origin. Pluripotent stem cells are the descendants of totipotent cells and can differentiate into cells derived from the three germ layers. These cells are typically cells in a stem cell line capable of differentiating into several different, final differentiated cell types. Multipotent stem cells can produce only cells of a closely related family of cells (e.g., hematopoietic stem cells differentiate into red blood cells, white blood cells, platelets, etc.). Unipotent cells can produce only one cell type, but have the property of self-renewal which distinguishes them from non-stem cells. Pluripotent, multipotent, and unipotent stem cells can originate from various tissue or organ systems, including, but not limited to, blood, nerve, muscle, skin, gut, bone, kidney, liver, pancreas, thymus, and the like.

As mentioned above, the Wnt and BMP signaling pathways are involved in the proliferation or differentiation of various stem cells. See e.g., Reya et al., Nature. 2005 Apr. 14; 434(7035):843-50. As a key component, Xom/Hom plays an important role in the preservation, expansion, and differentiation of the stem cells. Thus, Xom/Hom can be used in regulating development and differentiation of the stem cells, and in treating related proliferative or degenerative diseases. For example, Xom/Hom may function in slowing down or preventing differentiation of stem cells and, thereby, maintains a stem cell pool. It follows that an antagonist (i.e., inhibitor) of Xom/Hom can be used to promoting differentiation.

Dysregulation of this differentiation process results in various disorders, such as MDS. MDS are thought to arise from mutations in the multi-potent bone marrow stem cell. Differentiation of blood precursor cells is impaired, and there is a significant increase in levels of cell death apoptosis in bone marrow cells. Clonal expansion of the abnormal cells results in the production of cells which have lost the ability to differentiate. The progression of MDS to leukemia is a good example of the multi-step theory of carcinogenesis in which a series of mutations occur in an initially normal cell and transform it into a cancer cell. As described above, over expression of Hom/Xom in a MDS patient may lead to the blockage of the differentiation progress and apoptosis seen in MDS. Thus, an inhibitor of Hom/Xom can be used to treat MDS. Examples of the inhibitor include antibodies, antisense nucleic acids, RNAi agents, and small molecular compounds that specifically target Hom/Xom.

The treatment method of this invention can be used to treat the Myelodysplastic syndromes by promoting cell differentiation.

The method of this invention can also be used to treat or slow down the progress of other proliferative or degenerative disorders. Examples of the disorders include macular degeneration, neuron degeneration, Huntington's Disease, Parkinson's, Disease, Alzheimer's Disease and, Schizophrenia.

The terms "proliferation" and "expansion" as used interchangeably herein with reference to cells, refer to an increase in the number of cells of the same type by division. The term "differentiation" refers to a developmental process whereby cells become specialized for a particular function, for example, where cells acquire one or more morphological characteristics and/or functions different from that of the initial cell type. The term "differentiation" includes both lineage commitment and terminal differentiation processes. Differentiation may be assessed, for example, by monitoring the presence or absence of lineage markers, using immunohistochemistry or other procedures known to a worker skilled in the art. Differentiated progeny cells derived from progenitor cells may be, but are not necessarily, related to the same germ layer or tissue as the source tissue of the stem cells. For example, neural progenitor cells and muscle progenitor cells can differentiate into hematopoietic cell lineages.

The terms "lineage commitment" and "specification," as used interchangeably herein, refer to the process a stem cell undergoes in which the stem cell gives rise to a progenitor cell committed to forming a particular limited range of differentiated cell types. Committed progenitor cells are often capable of self-renewal or cell division.

The term "terminal differentiation," as used herein, refers to the final differentiation of a cell into a mature, fully differentiated cell. For example, neural progenitor cells and muscle progenitor cells can differentiate into hematopoietic cell lineages, terminal differentiation of which leads to mature blood cells of a specific cell type. Usually, terminal differentiation is associated with-withdrawal from the cell cycle and cessation of proliferation. The term "progenitor cell," as used herein, refers to a cell that is committed to a particular cell lineage and which gives rise to cells of this lineage by a series of cell divisions. An example of a progenitor cell would be a myoblast, which is capable of differentiation to only one type of cell, but is itself not fully mature or fully differentiated.

Compositions

Within the scope of this invention is a composition that contains a suitable carrier and one or more of the compounds described above. The composition can be a pharmaceutical composition that contains a pharmaceutically acceptable carrier, a dietary composition that contains a dietarily acceptable suitable carrier, or a cosmetic composition that contains a cosmetically acceptable carrier.

Examples of a dietary composition of the present invention include an active compound described above. Examples of this compound include Hom/Xom polypeptide or a functional fragment thereof, retinoic acid, resveratrol, ellagic acid, aspirin, salicylic acid, emodin, and flavonoid, and derivatives of these compounds. The composition also includes, but is not limited to, foods, food additives, nutritional supplements, and pharmaceutical preparations. It may be in the form of tablets, suspensions, implants, solutions, emulsions, capsules, powders, syrups, liquid compositions, ointments, lotions, creams, pastes, gels, or the like.

As a dietary supplement, additional nutrients, such as minerals or amino acids, may be included. A dietary composition can also be a drink or food product. As used herein, the terms "drink" and "food" broadly refer to any kinds of liquid and solid/semi-solid materials, respectively, that are used for nourishing an animal, and for sustaining normal or accelerated growth of an animal including a human. Examples of the drink product include, but are not limited to, tea-based beverages, juice, coffee, and milk. Examples of the food product include jelly, cookies, cereals, chocolates, snack bars, herbal extracts, dairy products (e.g., ice cream, and yogurt), soy bean product (e.g., tofu), and rice products.

A composition of the present invention may include a carrier. Depending on the kind of the composition, a carrier may be a suitable dietary carrier or a pharmaceutically acceptable carrier. Examples of a pharmaceutically acceptable carrier include, but are not limited to, biocompatible vehicles, adjuvants, additives, and diluents to achieve a composition usable as a dosage form.

A "pharmaceutically acceptable carrier," after administered to or upon a subject, does not cause undesirable physiological effects. The carrier in the pharmaceutical composition must be "acceptable" also in the sense that it is compatible with the active ingredient and, preferably, capable of stabilizing it. One or more solubilizing agents can be utilized as pharmaceutical carriers for delivery of an active compound. Examples of other carriers include colloidal silicon oxide, magnesium stearate, cellulose, sodium lauryl sulfate, and D&C Yellow #10.

The above-described composition, in any of the forms described above, can be used for treating cellular proliferative disorders and inflammation-related disorders.

An "effective amount" refers to the amount of an active compound that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having an active compound can also be administered in the form of suppositories for rectal administration.

A topical composition contains a safe and effective amount of a dermatologically acceptable carrier suitable for application to the skin. Generally, a topical composition can be solid, semi-solid, cream, or liquid. It may be a cosmetic or dermatologic product in the form of an ointment, lotion, foam, cream, gel, or solution. Details about dermatologically acceptable carriers are provided below.

A composition of the present invention may be used alone or in combination with other biologically active ingredients. Alone or in combination with other active ingredients, it may be administered to a subject in a single dose or multiple doses over a period of time. Various administration patterns will be apparent to those skilled in the art. The dosage ranges for the administration of the composition are those large enough to produce the desired effect. The dosage should not be so large as to cause any adverse side effects, such as unwanted cross-reactions and the like. Generally, the dosage will vary with the age, weight, sex, condition, and extent of a condition in a subject, and the intended purpose. The dosage can be determined by one of skill in the art without undue experimentation. The dosage can be adjusted in the event of any counter indications, tolerance, or similar conditions. Those of skill in the art can readily evaluate such factors and, based on this information, determine the particular effective concentration of a composition of the present invention to be used for an intended purpose.

Also within the scope of this invention is a cosmetic composition that contains an active compound described above. Examples of this compound include Hom/Xom polypeptide or a functional fragment thereof. Examples also include retinoic acid, resveratrol, ellagic acid, aspirin, salicylic acid, emodin, and flavonoid, and derivatives of these compounds. This composition contains a safe and effective amount of a dermatologically acceptable carrier that is suitable for topical application to the skin. It enables an active compound and optional component to be delivered to the skin at an appropriate concentration(s). The carrier can thus act as a diluent, dispersant, solvent, or the like to ensure that the active materials are applied to and distributed evenly over the selected target at an appropriate concentration. The carrier can be solid, semi-solid, or liquid. Preferably, it is in the form of a lotion, a cream, or a gel, in particular one that has a sufficient thickness or yield point to prevent the active materials from sedimenting. The carrier can be inert or possess dermatological benefits of its own. It should also be physically and chemically compatible with the active components described herein, and should not unduly impair stability, efficacy, or other use benefits associated with the composition.

The type of carrier utilized in the cosmetic composition depends on the type of product form of the composition. A cosmetic composition may be made into a wide variety of product forms such as those known in the art. These include, but are not limited to, lotions, creams, gels, sticks, sprays, ointments, pastes, and mousses. These product forms may comprise several types of carriers including, but not limited to, solutions, aerosols, emulsions, gels, solids, and liposomes.

Preferred carriers can contain a dermatologically acceptable, hydrophilic diluent. Suitable hydrophilic diluents include water, organic hydrophilic diluents, such as $C_1$-$C_4$ monohydric alcohols and low molecular weight glycols and polyols (including propylene glycol, polyethylene glycol of, e.g., MW 200-600), polypropylene glycol of, e.g., MW 425-2025, glycerol, butylene glycol, 1,2,4-butanetriol, sorbitol esters, 1,2,6-hexanetriol, ethanol, iso-propanol, sorbitol esters, ethoxylated ethers, propoxylated ethers, and combinations thereof. The composition preferably comprises at least about 60% of the hydrophilic diluent.

Preferred carriers also contain an emulsion having a hydrophilic phase, especially an aqueous phase, and a hydrophobic phase, e.g., a lipid, oil, or oily material. As well known to one skilled in the art, the hydrophilic phase will be dispersed in the hydrophobic phase, or vice versa, to form respectively hydrophilic or hydrophobic dispersed and continuous phases, depending on the composition ingredients. The term "dispersed phase," a term well-known to one skilled in the art, refers to a phase that exists as small particles or droplets suspended in and surrounded by a continuous phase. The dispersed phase is also known as the internal or discontinuous phase. The emulsion may be or contain (e.g., in a triple or other multi-phase emulsion) an oil-in-water emulsion or a water-in-oil emulsion such as a water-in-silicone emulsion. Oil-in-water emulsions typically comprise from 1% to 50% (preferably 1% to 30%) of the dispersed hydrophobic phase and from 1% to 99% (preferably from 40% to 90%) of the continuous hydrophilic phase; water-in-oil emulsions typically comprise from 1% to 98% (preferably from 40% to 90%) of the dispersed hydrophilic phase and from 1% to 50% (preferably 1% to 30%) of the continuous hydrophobic phase. The emulsion may also comprise a gel network, such as that described in G. M. Eccleston, Application of Emulsion Stability Theories to Mobile and Semisolid O/W Emulsions, Cosmetics & Toiletries, Vol. 101, November 1996, pp. 73-92, incorporated herein by reference. Preferred compositions herein are oil-in-water emulsions.

Preferred examples of a cosmetic composition of this invention have an apparent viscosity of from about 5,000 to about 200,000 mPa·s (centipoise). For example, preferred lotions have an apparent viscosity of from about 10,000 to about 40,000 mPa·s; and preferred creams have an apparent viscosity of from about 30,000 to about 160,000 mPa·s. Apparent viscosity can be determined using a Brookfield DVII RV viscometer, spindle TD, at 5 rpm, or the equivalent thereof. The viscosity is determined on a composition after the composition has been allowed to stabilize following its preparation, generally at least 24 hours under conditions of 25° C.±1° C. and ambient pressure after preparation of the composition. Apparent viscosity is measured with the composition at a temperature of 25° C.±1° C., after 30 seconds spindle rotation.

The cosmetic composition of the present invention is usually formulated to have a pH of 9.5 or below and in general have a pH in the range from 4.5 to 9, more preferably from 5 to 8.5. Some examples, particularly those containing an additional active agent such as salicylic acid, require a lower pH in order for the additional active to be fully efficacious. These compositions are usually formulated to have a pH of from 2.5 to 5, more preferably from 2.7 to 4.

The cosmetic composition may contain a wide variety of optional components, provided that such optional components are physically and chemically compatible with the essential components described herein, and do not unduly impair stability, efficacy, or other use benefits associated with the compositions. Optional components may be dispersed, dissolved, or the like in the carrier of the present compositions.

Exemplary optional components include emollients, oil absorbents, antimicrobial agents, binders, buffering agents, denaturants, cosmetic astringents, external analgesics, film formers, humectants, opacifying agents, perfumes, pigments, skin soothing and healing agents, preservatives, propellants, skin penetration enhancers, solvents, suspending agents, emulsifiers, cleansing agents, thickening agents, solubilising agents, waxes, sunscreens, sunless tanning agents, antioxidants and/or radical scavengers, chelating agents, anti-acne agents, anti-inflammatory agents, desquamation agents/exfoliants, organic hydroxy acids, vitamins, and natural extracts. Examples of such materials are described in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker., Inc.; in The Chemistry and Manufacture of Cosmetics, 2nd. Ed., deNavarre (Van Nostrand 1962-1965); and in The Handbook of Cosmetic Science and Technology, 1st Ed. Knowlton & Pearce (Elsevier 1993) can also be used in the present invention.

The cosmetic composition of the present invention is generally prepared by conventional methods known in the art of making topical compositions. Such methods typically involve mixing of the ingredients in one or more steps to a relatively uniform state, with or without heating, cooling, application of vacuum, and the like.

The cosmetic composition is useful for regulating or improving skin condition, including regulating visible or tactile wrinkles or discontinuities in skin, e.g., visible or tactile wrinkles or discontinuities in skin texture or color, more especially those associated with skin inflammation, ageing, or other internal factors (e.g., biochemical changes from within the skin) or external factors (e.g., ultraviolet radiation, environmental pollution, wind, heat, low humidity, harsh surfactants, and abrasives).

Regulating skin conditions can be carried out prophylactically or therapeutically. Prophylactical regulation includes delaying, minimizing, or preventing visible or tactile, swellings, wrinkles or discontinuities in skin. Therapeutic regulation, on the other hand, includes ameliorating, diminishing, minimizing or effacing such swellings, wrinkles or discontinuities. Regulating skin conditions involves improving skin appearance feel, e.g., providing a smoother, more even appearance or feel and reducing signs of aging.

A cosmetic composition is topically applied to the skin in a safe and effective amount. The applied amount, the frequency of application, and the period of use vary widely depending upon the active levels of a given composition and the level of regulation desired. Typically, the composition can be applied once per day. However application rates can vary from about once per week up to about three times per day or more.

The cosmetic composition of this invention provides visible improvement in skin condition essentially immediately following application of the composition to the skin. Such immediate improvement involves covering or masking skin imperfections such as textural discontinuities (including those associated with skin inflammation or aging, e.g., enlarged pores), or providing a more even skin tone or color. The composition also provides visible improvement in skin condition following chronic topical application, e.g., one week, one year, or the subject's life time.

Regulating skin conditions is preferably performed by applying a composition in the form of a skin lotion, cream, cosmetic, or the like which is intended to be left on the skin for an extended period for some aesthetic, prophylactic, therapeutic or other benefits, i.e., a "leave-on" composition. After applying the composition to the skin, the "leave-on" composition is preferably left on the skin for a period of at least 15 minutes and up to 12 hours.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Example 1

Experimental Procedures

Preparation of *Xenopus* embryos, microinjection, and luciferase assays—Protocols for handling embryos and for luciferase assays were essentially as described in Zhu et al., 2002, Dev Cell 3, 557-568. For a typical cellular luciferase assay, $2\times10^5$ cells were split into 12-well cell-culture plates and incubated for 24 hours and then transfected with 3 of liposome transfection reagent (TransIT1, Mirus), 1 µg of DNA plasmids of selected genes, and 0.3 µg of reporter plasmids (Hela cells require one third while 293T cells require one sixth of the DNA and liposome amount). At 48 hours post-transfection, the cells were washed with PBS, lysed with 1× cell lysis buffer (Promega cell lysis buffer), scraped, and collected. After incubation on ice for 30 minutes, the cells were cleared by centrifugation at 12,000 g for 15 seconds and transferred to a new tube; then 20 µl of the cell lysate was mixed with 100 µl of Luciferase Assay reagent (Promega), and the luciferase activity was measured by scintillation counting.

Plasmids and recombinant proteins—*Xenopus* LEF1, LEF1ΔHMG, LEF1Δ60, LEF1Δ160, Xom, and its deletion mutants were subcloned by the polymerase chain reaction base technique into the pCS2+ and PGEX4T3 vectors and verified by in vitro translation and sequencing. pGL3-OT and pGL3-OF were generous gifts from Dr. B Volgestein; p2.4BMP4-Luc was a generous gift from Dr. J Feng; pGL3 promoter MSX2 (WT) and pGL3 promoter MSX2-SDM-600/-766 were generous gifts from Dr. C Sirard.

Preparation of nuclear and cytoplasmic extracts—Cells ($4\times10^6$) were trypsinized and washed twice with PBS and pelleted by centrifugation. Total protein was obtained by lysing the cells in 150 µl of RIPA buffer (150 mM NaCl, 1% NP40, 0.5% DOC, 0.1% SDS, 50 mM Tris pH8.0) containing 1× proteinase inhibitors (Roche, proteinase inhibitor cocktail). Cytoplasmic proteins were obtained by incubation of $2\times10^6$ cells with 150 µl of hypotonic buffer (0.05% NP40, 10 mM HEPES pH7.9, 1.5 mM $MgCl_2$, 10 mM KCl, 1 mM DTT) containing 1× proteinase inhibitors on ice for 10 minutes and then centrifuged at 4000 rpm for 2 minutes. The supernatants were collected and used as cytoplasmic proteins. The nuclear pellets were washed twice with PBS. Nuclear proteins were obtained by incubating the pellet on ice for 60 minutes in 150 µl of RIPA buffer. Levels of β-catenin in fractioned cellular extracts were determined by western blotting using specific antibody (Takara Bio).

GST pull-down assay—Five micrograms of GST fusion proteins and 5 µl of $^{35}$S-labeled IVT proteins were mixed with 20 µl of 50% glutathione Sepharose 4B beads in 500 µl of binding buffer (50 mM Tris pH 8.0, 100 mM NaCl, 50 mM KCl, 5 mM $MgCl_2$, 1 mM DTT, 10% glycerol and 0.2% NP40). The mixtures were incubated at 4° C. for 3 hours and washed with 1×PBS plus 0.2% NP40 four times. Bound material was released with 2× sample buffer, boiled at 95° C. for 5 min, centrifuged briefly, and revealed by SDS-PAGE and autoradiography.

Co-immunoprecipitation—The affinity-protein G beads were prepared by mixing 20 µl of protein G plus-Agarose beads (Santa Cruz Biotechnology) with 1 µg of corresponding antibody. A total of $2\times10^6$ of cells were lysed with 1× cell lysis buffer (Promega) containing 1× protease inhibitor reagent (Roche), incubated on ice for 30 minutes, sonicated briefly, and centrifuged at 12,000 g for 5 minutes at 4° C. The supernatants were further cleaned with 20 µl of untreated protein G plus-Agarose beads and 2 µg of pre-immune serum for 2 hours at 4° C. The supernatants were then mixed with 20 µl of prelabeled protein G plus-Agarose beads at 4° C. overnight. The beads were washed four times with PBS plus 0.2% NP40. Bound proteins were released by 2× sample buffer, boiled at 95° C. for 5 minutes centrifuged briefly, and revealed by western-blot analysis with specific antibodies.

Histological staining—Embryos were fixed with 3.7% formaldehyde, 0.1 M MOPS (pH 7.4), 2 mM EGTA, and 1 mM $MgSO_2$ at indicated stages. The embryos were then embedded in paraffin and sectioned at a 10-µm thickness. The sections were stained with hematoxylin and eosin (H&E), and subjected to histological analysis. The sections were further stained with 2 µg/ml of 4',6-diamidino-2-phenylindole, dihydrochloride (DAPI) (Invitrogen), to reveal the nucleus of the embryonic cells.

Analysis of gene expression by real-time PCR—Total RNA was extracted by Trisol methods. Eight embryos from each treatment group were pooled and Homogenized in 1 ml of Trizol (Invitrogen). Chloroform (200 µl) was then added to the sample. After vortex mixing, the samples were centrifuged at 12,000 rpm for 1 minute and the supernatants were collected in new tubes. Isoproponol (500 µl) was added to each sample, mixed, and kept at RT for 10 minutes. Samples were then centrifuged for 30 minutes. The pellets were washed twice with 70% ethanol, air dried, and suspended in 100 µl of $ddH_2O$. The final RNA concentration was determined by measurement at $OD_{260}$. First-strand cDNA was synthesized with the SuperScript first-strand synthesis system (Invitrogen) according to the manufacturer's protocol. Briefly, 2.5 µg of total RNA from each sample was used. The final volume of the RT product was 20 µl and was diluted to 200 µl (10× dilution); 8 µl of the diluted RT product was used for real-time PCR using LightCycler System (Roche) and LightCycler FastStart DNA Master SYBR Green I, according to manufacturer's instructions. The relative levels of gene expression were calculated by the formula: relative gene expression=2–ΔCd (ΔCd=cycle of the specific gene—cycle of the reference Histone-4 gene). Each sample was done in triplicate. The sequences of the primers are available upon request.

Results

Xom transactivates LEF1/TCF-mediated transcription—Xom is a major ventral cell fate determination factor of the BMP4 signaling pathway. Using the TOPflash assay, a previous investigation located LEF1/TCF-mediated transcriptional activities in the ventral-posterior side of embryos (Kiecker et al., 2001, Development 128, 4189-4201. By injecting TOPflash plasmid into the two ventral blastomeres at the 4-cell stage and examining luciferase activities during gastrulation stage, it was confirmed the LEF1/TCF-mediated transcriptional activities on the ventral side of embryos during early embryogenesis (the pGL3-OT, which contains three copies of the optimal TCF binding motif, was a generous gift from Dr. B Vogelstein. To explore a potential inter-relationship between Xom expression and LEF/TCF-mediated transcription, the effect of Xom expression on LEF1/TCF-mediated transcription was examined using the TOPflash-luciferase assay. When mRNA encoding Xom was co-injected with the TOPflash reporter construct into *Xenopus* embryos at the two-cell stage, expression of Xom enhanced the TOPflash reporter transcriptions sevenfold as compared with its expression in embryos injected with a construct of TOPflash alone. The trans-activating effect of Xom on the TOPflash reporter was specific, since expression of Xom did not activate the control FOPflash reporter (pGL3-OF, also a gift from Dr. Vogelstein) which contains mutations at the LEF/TCF binding sites). To determine whether Xom transaction of LEF1/TCF-mediated transcription is context-dependent in embryos, the effect of Xom expression on LEF1/TCF-mediated transcription in non-embryonic cells was also studied. When plasmids encoding Xom and TOPflash were co-transfected into HeLa and HCT116 cells (and later 293T cells), Xom expression induced the transcription of the TOPflash constructs in these non-embryonic mammalian cells, indicating that Xom exerts a general induction effect on LEF1/TCF-mediated transcription. Again, the specificity of Xom transactivates LEF1/TCF-mediated transcription was indicated by the finding that Xom failed to activate the FOPflash reporter construct in these tissue culture experiments.

Xom binds to LEF1/TCF factors in vivo and in vitro-Binding of LEF1/TCFs to the promoter of TOPflash is required for the activation of the reporter construct; thus, the finding that expression of Xom activates TOPflash but not FOPflash raised the possibility that Xom activates the TOPflash reporter through interaction with LEF/TCFs. This hypothesis was tested by determining whether Xom physically interacts with LEF1/TCFs. Co-immunoprecipitation experiments was carried out in HCT116 cells transiently transfected with myc-Xom. It was found that immunoprecipitation of endogenous TCF4 with anti-TCF4 antibodies co-precipitated the Xom protein. The in vivo association between Xom and TCF4 appears to be strong and could not be dissociated with 300 mM NaCl and 0.1% NP40. To determine the domain of Xom that mediates its interaction with LEF1/TCFs, serial deletion mutants of Xom were made and tested for their interactions with TCF4 in vivo. The proteins used were: wild type Xom (aa 1-326), XomND55 (aa. 56-326), Xom ND175 (aa. 176-326), XomCD145 (aa. 1-181), XomCD85 (aa. 1-241), and XomID110 (fusion of aa 1-130 and aa 241-326). All Xom mutants that carry the Homeobox region co-immuno-precipitated with anti-TCF4 beads, while those lacking the Homeodomain did not.

These data indicate that the Homeodomain of Xom plays a critical role in mediating complex formation between Xom and LEF1/TCF factors. Following the demonstration of complex formation between Xom and TCF4 in vivo, the critical domains of LEF1/TCFs involved in the interaction with Xom were identified. At least four members of the LEF1/TCF family have been identified in vertebrates (LEF1, TCF1, TCT3, and TCF4), and LEF1 shows an expression pattern similar to that of Xom. Zygotic transcription of LEF1 starts after the onset of the MBT and is enriched at the ventral-caudal side of the animal (Molenaar et al., 1998, Mech Dev 75, 151-154). Genetic data indicate that LEF1 is essential for ventral-posterior patterning (Roel et al., 2002, Curr Biol 12, 1941-1945), making LEF1 a potential candidate as the Xom-interacting protein. It was therefore tested whether Xom interacts with LEF1 and explored the critical domain of LEF1 involved in the interaction through deletion mutagenesis analysis.

It was found that very few cells co-expressed Xom and full-length LEF1; therefore. The potential interaction between Xom and LEF1 was then examined through an in vitro binding assay. When in vitro translation (IVT) products of $^{35}$S-labeled LEF1 or its deletion mutants were mixed with GST-Xom or GST alone, LEF1 was pulled down by GST-Xom but not by the control GST. The C-terminal—deleted mutant LEF1ΔHMG appeared to have much less affinity for Xom, whereas the N-terminal—deleted mutant of LEF1Δ60 and LEF1Δ160 bound to GST-Xom as effectively as did the wild-type LEF1. Thus, the interaction between Xom and LEF1 appears to be dependent on the LEF1 C-terminal motif, a supposition further supported by a LEF1/TCF transactivation assay.

To determine the potential physiological relevance of Xom transactivation of LEF1/TCF-mediated transcription, the effect of Xom on the expression of BMP4 downstream genes was examined, using promoter-luciferase analysis. The Msx2 gene is downstream of BMP4, whose promoter contains both an LEF1/TCF binding site and a BMP4-responsive element (SBE) (Hussein et al., 2003, J Biol Chem 278, 48805-48814). Consistent with the potential direct involvement of LEF1/TCFs in BMP/Xom signaling, it was found that Xom activated both the wild-type Msx2 promoter and the SBE-mutated Msx2 promoter that retain only functional LEF1/TCF binding sites.

Xom transactivates LEF1/TCF-meidated transcription is not mediated through β-catenin accumulation—Previous studies have shown that LEF1/TCF-mediated transcription is activated by β-catenin (Behrens et al., 1996, Nature 382, 638-642;

Huber et al., 1996, Mech Dev 59, 3-10; Molenaar et al., 1996, Cell 86, 391-399). To explore the mechanism of Xom activation of LEF1/TCF-mediated transcription and to rule out the possibility that Xom transactivation of LEF1/TCF-mediated transcription is through an increase in β-catenin protein level or nuclear translocation, the effect of Xom expression on the protein level and intracellular distribution of β-catenin was examined in HCT116 cells.

It was found that, whereas Xom expression activates LEF1/TCF-mediated transcription in a concentration-dependent manner, there is no corresponding increase (rather a small decrease) in the level of total intracellular β-catenin protein. In addition, when the total intracellular proteins were fractionated into the cytoplasmic and nuclear portions, no significant nuclear shifts of β-catenin were observed upon Xom expression (again, rather a small decrease). It was also found that, the domain of LEF1 that interacts with Xom locates at the C-terminal region of the LEF1, which is separated from the N-terminal domain involved in interaction with β-catenin. It was found that the LEF1Δ60, a dominant negative LEF1 mutant that blocks β-catenin transactivation of LEF1/TCF-mediated transcription, promotes Xom transactivation of the LEF1/TCF-mediated transcription in TOPFlash assay. This is consistent with the possibilities that Xom transactivation of LEF1/TCF-mediated transcription through direct interaction.

Xom transactivates LEF1/TCFs through its N-terminal TAD—The interaction between Xom and LEF1 allowed us to further explored the molecular mechanism of Xom transactivation of LEF1/TCF-mediated transcription. Previous studies have shown that β-catenin binds to TCFs through its central Armadillo repeats but activates TCFs through its C-terminal motif (van de Wetering et al., 1997, Cell 88, 789-799 and Orsulic et al., 1996, J Cell Biol 134, 1283-1300). Therefore, after identifying the critical domain of Xom involved in LEF1/TCF interaction, the functional domain of Xom involved in LEF1/TCF transactivation it was further analyzed. When cDNA encoding Xom or its deletion mutants was co-transfected with the reporter construct of TOPflash into 293T cells, expression of both Xom and its C-terminal deletion mutant XomCD85 activated the TOPflash almost 10-fold more than did the control cells transfected with TOPflash only. In comparison, the ability to activate the LEF1/TCF-mediated transcription was significantly diminished in the N-terminal—deleted mutants of Xom, the XomND55 and XomND175. The XomND175 in particular retains little if any ability to transactivate the LEF1/TCF-mediated transcription. Consistent with a model of Xom transactivates LEF1/TCF-mediated transcription through direct interaction, it was found that Xom mutant that lack the LEF1/TCF-interaction motif failed to activate LEF1/TCF-mediated transcription during early embryogenesis. Xom is a known transcriptional repressor of dorsal gene expression. To determine whether the dual transcriptional function of Xom is independent of each other, the effect of these Xom deletion mutants on dorsal gene expression was further examined. When mRNA encoding Xom and its deletion mutants were co-injected with mRNA encoding Activin and Gsc-promoter-luciferase construct into the embryos at the two-cell stage, both the N-terminal—deleted mutants and the C-terminal—deleted mutants of Xom strongly inhibited Activin-induced activation of the Gsc-promoter. These data indicated that the function of Xom transactivation domain is independent of the Xom repressor function, and that the Xom transactivation domain (TAD) resides in its N-terminal region, which was further supported with TOPflash assay during early embryogenesis.

Xom N-terminal TAD is required for ventral signaling—Xom is emerging as an essential cell fate determination factor during mesoderm differentiation to promote the expression of ventral specific genes (Koide et al., 2005, Proc Natl Acad Sci USA 102, 4943-4948). It has been proposed that Xom forms a positive re-enforcement loop with BMP4 to promote ventral cell fate (Schmidt et al., 1996, Development 122, 1711-1721). To determine whether the Xom N-terminal TAD plays a role in Xom transactivation of ventral specific genes, the effect of XomND175 on transactivation of the BMP4 promoter during early embryogenesis was examined (the BMP4-luciferase construct was a generous gift of Dr. J. Feng (Zhang et al., 2002, Biochem Biophys Res Commun 293, 1412-1419 and Ogawa et al., 2006, J Biol Chem 281, 18363-18369). It was found that, in contrast to Xom, XomND 175 failed to transactivate the BMP4 promoter. Moreover, in comparison with the luciferase activities in control embryos, embryos injected with XomND 175 revealed less luciferase activities, suggesting that expression of XomND175 exerts a dominant-negative effect to block the activity of endogenous Xom. To further determine the effect of Xom TAD on the expression of downstream genes, each of the two blastomeres of embryos at the two-cell stage was injected with mRNA encoding Xom or XomND175. The embryos were allowed to develop until the gastrula stage (stage 10.5) and total mRNAs were extracted from the injected embryos and non-injected control embryos. The levels of BMP4 and Xom expression were determined by Q-PCR, using Histone-4 as an internal control. Consistent with its role in transactivation of ventral gene expression, expression of wild-type Xom increased the expression of BMP4. In contrast, expression of XomND175 failed to enhance the expression of BMP4, suggesting that the Xom TAD is required for its transactivation of BMP4 expression. Moreover, consistent with the disruption of the positive auto feedback loop of BMP4 and Xom, expression of XomND175 exerted a strong inhibitory effect on the expression of Xom itself. Together with the notion that LEF1/TCF binding sites on the promoters of ventral specific genes are required for their responsiveness to BMP4 signaling and that loss of function of LEF1 leads to ventral defects (Roel et al., 2002, Curr Biol 12, 1941-1945 and Karaulanov et al., 2004, Embo J 23, 844-856), our findings suggest that Xom trans-activation of LEF1/TCF-mediated transcription is likely to play a critical role in ventral signaling and ventral cell fate determination.

Xom transactivation of LEF1/TCFs is essential for gastrulation—Our biochemical and mutagenesis studies revealed that Xom possesses a LEF1/TCF-transactivation domain in its N-terminal region. It was identified that a Xom mutant, XomND175 possessed negligible LEF1/TCF-transactivation ability but retains transcriptional repressor function. To determine the potential physiological function of Xom transactivation of LEF1/TCF-mediated transcription during early embryogenesis, the loss-of-function approach was used to explore the effect of XomND 175 expression on embryogenesis. The mRNAs encoding Xom, XomND175, and other Xom deletion mutants were injected into one of the two ventral blastomeres at the four-cell stage as indicated. It was observed that embryos injected with mRNA of XomND175 but not other Xom mutants showed catastrophic effects during gastrulation. In addition to the mutant specificity phenotype of XomND175, the XomND175 effects appeared to be stage-specific. Unlike XomND175-mRNA, XomND175-cDNA caused little, if any, abnormalities during gastrulation. Closer inspection showed that the embryos injected with XomND 175 mRNA progressed through the cleavage and pregastrulation stages; however, as gastrulation begins, many large whitish gray-colored cells appear in the injected side. As gastrulation proceeds, these cells gradually lose a defined cellular appearance, giving the embryos a "rotten" appearance. To define the cellular and histological changes associated with XomND175 expression, the XomND175-mRNA—injected and control embryos was fixed, sliced them into 10-μM thin sections, and stained them with H&E and DAPI. Little histological change was associated with ND175 expression at the cleavage and pregastrulation stages, but many large rounded-up structures were seen at the gastrulation stage, which appeared to be dead cells. None of these large rounded-up structures in ND175-injected embryos stained with DAPI, suggesting that they had lost normal cellular structures, such as the nucleus. The embryos appeared to be very sensitive to the effect of XomND175. The 50% effective penetration rate was achieved with less than 50 pg of XomND175 mRNA (data not shown). The finding that expression of a dominant-negative Xom mutant that lacks TAD led to embryonic arrest at the gastrulation stage suggests that Xom transactivation of LEF1/TCF-mediated transcription is essential for gastrulation. Similar findings have been noted for other BMP4 related transcriptional factors, such as Bix3 (Trindade et al., 2003, Development 130, 4611-4622)

Example 2

To explore the intracellular interaction of Xom and LEF1 and its potential cellular effect, the intracellular distribution and effect of Xom in the presence or absence of LEF1 in Hela cells was studied by standard methods. It was found that the wild-type Xom to concentrates in nuclei in transfected Hela cells. However, when Xom and LEF1 were co-transfected into Hela cells, very few cells expressed both proteins. The few cells that co-express Xom and LEF1 frequently contain giant, multi-lobular nuclei, indicating a growth-arrest effect of co-expression of Xom and LEF1.

To prove that the growth inhibition effect of Xom is mediated through functional interaction with LEF1, Xom was co-transfected with dominant negative LEF1 (LEF1ΔHMG) into Hela cells. It was found that many transfected cells co-expressed both Xom and LEF1ΔHMG, indicating that the growth-arrest effect of Xom is mediated through functional interaction with LEF1.

This hypothesis was further tested using a GFP and MTA cell-viability assay. Briefly, 5×104 cells were plated onto a 96-well cell culture plate. 24 hours after plating, cells were transfected with 0.3□μl of TransIT-1 and 0.1 μg of plasmid DNA. 36 hours after transfection, cell viability was measured with CellTiter 96 Aqueous No-radioactive Cell Proliferation Assay kit (Promega). Each transfection was repeated four times to reduce the experimental variation. The results indicated that co-expression of Xom and LEF1 significantly reduced the viability of transfected Hela cells. Consistent with the idea that a functional interaction between Xom and LEF1 is important for Xom effect on cell fate, the growth-arrest phenotype was attenuated in cells co-expressing Xom and LEF1 (ΔHMG).

The level of activated caspase3 in cells transfected with Xom and LEF1 or LEF1ΔHMG was examined to explore whether the cellular growth-arrest effect of the interaction of Xom and LEF1 relates to caspase activation. It was found that expression of Xom and Xom/LEF increased the levels of activated caspase3, an effect that can be blocked by the apoptosis inhibitor ZVAD. The effect of Xom on caspase3 activation was blocked by co-expression of LEFΔHMG, suggesting that a functional interaction between Xom and LEF1 is required for the activation of apoptosis. The pro-apoptotic activation of LEF1 by Xom appears to be opposite the anti-apoptotic role of LEF1/TCF activation by β-catenin.

BMP4/Xom is key regulators of dorsoventral patterning. Although previous investigations define the role of LEF1/TCFs in dorsal development, the interaction between LEF1/TCF and Xom suggests that LEF1/TCF plays a role in mediating the signaling of the BMP4/Xom pathway during ventralization. To test this hypothesis, it was explored whether LEF1 potentiate the ventralizing effect of Xom. When a low level of Xom or LEF1 was expressed in the dorsal blastomeres, little discernable ventralizing effect was detected. However, co-expression of the Xom and LEF1 at the same concentration leads to significant dorsal inhibition. Consistent with these findings, it was found that the expression of LEF1 alone results in mild inhibition of dorsal development in a dosage-dependent manner. To determine the specificity of the function of LEF1 in mediating Xom signaling, the effect of the expression of dominant negative LEF1 (ΔHMG) on the ventralizing effect of Xom was explored. It was found that expression of ΔHMG rescued the ventralized phenotype resulted from overexpression of high level of Xom, while expression of ΔHMG alone at the dorsal blastomeres induced little discernable changes.

The above results indicate that the LEF1/TCF family of transcriptional factors, previously known as the mediator of the Wnt/β-catenin pathway, is also the executor of the BMP4/Xom pathway. Xom and β-catenin, therefore, may compete for LEF1/TCFs for their distinguished functions in cell fate determination. Previous studies have defined the role of LEF1/TCFs in anti-apoptosis and dorsal development in association with β-catenin of the Wnt pathway. Our current investigation indicates that association of LEF1/TCFs with Xom may lead to cell-growth arrest and ventral development. LEF1/TCFs therefore functions as the converging point of Xom/BMP4 and β-catenin/Wnt signaling to mediate their combined signaling effect on cell fate. Beyond competition for the same family of transcriptional factors for different phenotype and distinguished from Smads, it was found that Xom expression reduces β-catenin protein level and blocks β-catenin transactivation of LEF1/TCFs-mediated transcription. Given the implication of β-catenin transactivation of LEF1/TCFs in patterning formation and malignant transformation of a variety cancers, further investigation of the molecular mechanism underlying LEF1/TCFs-meidated cell fate determination of BMP/Xom are important for understanding the basic mechanism of embryogenesis and carry broad therapeutic implications in neogenesis and degenerative diseases.

During our investigation, it was discovered that new component of the BMP4 pathway is critical for cell-fate determination. On the basis of our discovery cited above, it was further discovered that BMP4 pathway utilizes the TCF/LEF1 transcriptional factors to transduce its signal. It was found that when combined together, expression of the LEF1/TCF factors and Xom (a component of the BMP4 pathway) induces cell death in colon cancer cells, with the efficacy of near 100% (Also effective in cervical cancer cells, prostate cancer cells)-gene therapy methods.

A human Xom homology, Hom, (previously known as the VentX2), was cloned by a standard method and subjected to the above assays. It was found that Hom functions in a similar way to the *Xenopus* Xom.

Xom stability is critical for cell-fate determination. While expression of wild-type Xom alone causes growth arrest in 30% colon cancer cells, expression of stable Xom causes growth arrest in 60% colon cancer cells.

The protein level of Xom is controlled by proteolysis, and is controlled by phosphorylation of Ser140/144. Methods and materials (e.g., specific phospho-antibodies) were developed to monitoring the Xom kinase activity, which can be used to screen for drugs effective for cancer prevention and treatment.

Example 3

As mentioned above, Hom is a human homologue of the vertebrate Xom. Biochemical studies showed that Hom binds to the LEF1/TCF-transcriptional factors and blocks LEF1/TCF transactivation by the oncogenic signaling of Wnt/β-catenin pathway. Hom locates on Chromosome 10q26, a region that is frequently deleted in metastatic cancers, such as metastatic colon cancer, suggesting a role of Hom in cancer formation and metastasis. To explore a potential role of Hom on cancer cell growth, Hom was transiently expressed in colon and lung cancer cells (HCT116 and H460 respectively) and the morphological changes associated with Hom expression studied.

Plasmids (0.5 to 2 µg) encoding GFP-Hom or GFP alone were transfected into HCT116 or H460 cells. At 36 hours post-transfection, the cells were fixed with paraformaldehyde. The morphological changes associated with GFP-Hom or GFP expression were examined with phase contrast or fluorescent microscope. It was found that expression of GFP-Hom caused a rounding-up phenotype in more than 80% of the colon and lung cancer cells that transiently expressing GFP-Xom. In contrast, less than 10% cells expressing GFP became rounding-up in this assay.

To further define the morphological changes associated with expression of GFP-Hom and determine whether the rounding-up phenotype is associated with cell growth arrest/death, TUNEL assay was performed on cancer cells transiently expressing GFP-Hom. HCT116 or H460 cells were transiently transfected with plasmid encoding GFP (vector) or GFP-Hom. Twenty-four hours post-transfection, the cells were collected and stained with Hoechst 33258 to reveal the nuclei. Cells with characteristic condensed chromatin and fragmented nuclei were scored as apoptotic cells. The percentage of cells that revealed apoptotic phenotype was determined by counting the apoptotic cells and cells with normal morphology. At least 400 cells were counted for each sample by random field selection. It was found that about 30% of HCT116 and H460 cells that transiently expressing GFP-Hom showed apoptotic figures, while about 5% cells in the control GFP group revealed apoptotic figure. This result suggested that expression of Hom induces cancer cell death.

The cell growth arrest effects of Hom on cancer cells were also confirmed by in vitro colony formation assay. It was found that expression of GFP-Hom led to 100% reduction in colony formation in colon cancer cells and lung cancer cells, as compared with control cells that expressed GFP.

The p53 is a critical cellular factor involves in tumor suppression. It has been shown that p53 co-operate with other tumor suppressor gene, such as the ARF to suppress tumor cell growth. Loss of function mutations of p53 is regarded as a major step during malignant transformation. To determine whether p53 may play a role in Hom suppression cancer cell growth, the effects of Hom in colon in which the p53 has been deleted or mutated were examined, using HCT116 p53−/− and H1299 respectively following the experimental procedures described above.

It was found that expression of GFP-Hom caused apoptotic figures in about 30% p53−/− colon and lung cancer cells, a figure similar to the colon and lung cancer cells that had wild-type p53. The results suggest that Hom triggered cell death in p53 independent manner. Thus, Hom may play a major tumor suppressor function in a large variety of cancer cells, in which the p53 is mutated.

The effect of Hom on colon cancer cell growth was examined in athymic nude mice to determine whether Hom may suppress tumor formation in vivo. Nude mice were purchased from Charles' River Laboratory. HCT116 cells was transiently transfected with a plasmid encoding GFP-Hom (GFP was used as an indicator of successful transfection). A control HCT116 was prepared by transfection with empty GFP-vector. For subcutaneous injection, $5 \times 10^6$ cells were prepared for each injection site. The cells were released from culture dishes with trypsin, which was inactivated afterwards with complete serum. The cells was then collected with gentle centrifugation at 400 g for 5 minutes and re-suspended with PBS to a final concentration of $5 \times 10^7$ cells/ml.

Two groups of tests were performed. In group 1, after transfection, the GFP-Hom or GFP transfected HCT116 cells were sorted from the non-transfected cells, using GFP as a marker for the sorting. In group 2, the transfected cells were used directly for injection without being sorted for GFP expression (with an estimated transfection efficiency of about 60%). A 1-cc syringe was used to inject the cells subcutaneously into nude mice at the shoulder level on the back after local sterilization with alcohol. For each site, 100 µl of cells, which contains $5 \times 10^6$ cells, were injected. The injected mice were ear tagged and observed daily for up to 21 days (It usually takes 7 to 10 days for tumors to develop in nude mice). After the morphological observation, the animals were sacrificed and the tumors dissected out. The cellular and structure abnormalities of the tumors was determined with HE staining and microscopic examination.

It was found that no tumors formed in nude mice injected with the sorted GFP-Hom-expressing HCT116 cells. In contrast, tumors were found in the control nude mice injected with HCT116 cells that were transfected with GFP-vector alone. Similarly, nude mice injected with the unsorted GFP-Hom-expressing HCT116 cells had tumors, but had about 60% reduction in tumor size as compared with the control nude mice, which were injected with HCT116 cells transfected with GFP only. These results support that Hom inhibited tumorigensis.

To determine whether Hom expression affects cell proliferation and survival in vivo, the tumor samples were sectioned and subjected to TUNEL assays, where BrdU triphosphate may be incorporated into the 3'-hydroxyl ends of DNA fragments (a hallmark of apoptosis) by the terminal deoxynucleotidyl transferase (TdT). The BrdU incorporation can be detected by fluorescently labeled anti-BrdU antibodies. The TUNEL assays showed active apoptosis in tumor cells expressing the GFP-Hom, while little apoptosis was detected in the tumor cells that expressing GFP only.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. A method of assessing a human subject's cancer prognosis, the method comprising:
   obtaining a cell from the subject;
   determining in the cell the level of a kinase activity, wherein the kinase activity is phosphorylation of Ser140 or Ser144 of an exogenous Xom polypeptide;
   whereby the subject is determined to have a bad prognosis if the level of the kinase activity is higher than a control level.

2. The method of claim 1, wherein the determining step is carried out by: (1) obtaining an extract of the cell; (2) contacting the extract with a polypeptide containing a fragment of Xom that includes Ser140 or Ser144 of Xom; and (3) determining the phosphorylation level of the Ser140 or the Ser144.

3. The method of claim 2, wherein the polypeptide contains a fragment of SEQ ID NO:7.

4. The method of claim 3, wherein the polypeptide contains the sequence of SEQ ID NO:13, 14, or 17.

5. The method of claim 2, wherein the polypeptide contains the sequence of SEQ ID NO:7.

6. The method of claim 2, wherein step (3) is carried out by an antibody that specifically recognizes phosphorylated Ser140 or phosphorylated Ser144 of Xom.

7. The method of claim 6, wherein the polypeptide contains the sequence of SEQ ID NO:7.

8. The method of claim 1, wherein the determining step is carried out by: (1) expressing in the cell a polypeptide containing a fragment of Xom that includes Ser140 or Ser144 of Xom; and (2) determining the phosphorylation level of the Ser140 or the Ser144.

9. The method of claim 8, wherein the polypeptide contains a fragment of SEQ ID NO:7.

10. The method of claim 9, wherein the polypeptide contains the sequence of SEQ ID NO:13, 14, or 17.

11. The method of claim 8, wherein the polypeptide contains the sequence of SEQ ID NO:7.

12. The method of claim 8, wherein step (2) is carried out by an antibody that specifically recognizes phosphorylated Ser140 or phosphorylated Ser144 of Xom.

13. The method of claim 12, wherein the polypeptide contains the sequence of SEQ ID NO:7.

14. The method of claim 1, wherein the cell is a cancer cell.

15. The method of claim 1, wherein the cell is obtained from the subject before, during, or after a cancer treatment is administered to the subject.

* * * * *

SEQUENCE LISTING

<160> NUMBER OF SEQ ID NOS: 17

<210> SEQ ID NO 1
<211> LENGTH: 59
<212> TYPE: PRT
<213> ORGANISM: Homo sapiens

<400> SEQUENCE: 1

Arg Val Arg Thr Ala Phe Thr Met Glu Gln Val Arg Thr Leu Glu Gly
1               5                   10                  15

Val Phe Gln His His Gln Tyr Leu Ser Pro Leu Glu Arg Lys Arg Leu
            20                  25                  30

Ala Arg Glu Met Gln Leu Ser Glu Val Gln Ile Lys Thr Trp Phe Gln
        35                  40                  45

Asn Arg Arg Met Lys His Lys Arg Gln Met Gln
    50                  55

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Asp Ser Gly Tyr Glu Ser Glu Thr Ser Cys
1               5                   10

<210> SEQ ID NO 3
<211> LENGTH: 60
<212> TYPE: PRT
<213> ORGANISM: Homo sapiens

<400> SEQUENCE: 3

Ser Ser Arg Leu Arg Thr Ala Phe Thr Ser Asp Gln Ile Ser Thr Leu
1               5                   10                  15

Glu Lys Thr Phe Gln Lys His Arg Tyr Leu Gly Ala Ser Glu Arg Gln
            20                  25                  30

Lys Leu Ala Ala Lys Leu Gln Leu Ser Glu Val Gln Ile Lys Thr Trp
        35                  40                  45

Phe Gln Asn Arg Arg Met Lys Tyr Lys Arg Glu Ile
    50                  55                  60

<210> SEQ ID NO 4
<211> LENGTH: 993
<212> TYPE: DNA
<213> ORGANISM: Homo sapiens

<400> SEQUENCE: 4
gacaagatga ctaaagcttt ctcctctgtt gaatggcttg ctcaaagcag ccgcagatct      60
cacagagagc agccaagcaa agtggatcag agatattcac cgtaccccag gccatccctg     120
ccttcctgga cagtgatgt gtccccttct tcatggaaca gccaactatc tccagatcca     180
gacagtgccc aagtctcacc atgccctgtg agtgcacaag tatctccata ttcctcagac     240
agtgaaatat cactgtattc acatgaagaa gaagcctctt tctatggaat ggactttaat     300
acatcatcat cccctggaga caatggattg ctacacaggg acacaacctc atactccaga     360
ggaatggagg ccatgtcggc cagcactcca gcaacatcac ctgtgaaagg ggcacaacct     420
gttgattccg cctacagcac tagcactgac tcaggctatg aaagtgaaac gagtcgatcc     480
aactctacag cccctgaagg agatgcctcc gtatctctga gtcccaatga tacctcagat     540
gaagagggca agatgggccg aaggttgagg acggctttca ccagtgatca gatctccact     600
ctggagaaga cttttcagaa acacagatac cttggggcgt ctgaaagacg gaaactcgca     660

```
gccaaactcc agctttctga agtccagatt aaaacttggt tccagaaccg caggatgaaa      720
tacaaacggg aaatccaaga tggcagacca gactcatacc acccagccca gttctttggt      780
gtgtacggct atgcacagca gcccactcct gtattccagc atgcagtcca acatccctac      840
ccaggttata acccactaat ggaaaccctg cctggtacca tgccctatac catgcatcca      900
cctgccatgg actctctgac tcccttcaac tctcaacctt ttcagatgct ctacctgccc      960
caacagcacc ttgggcaacc tctggcctat tag                                   993
```

<210> SEQ ID NO 5
<211> LENGTH: 258
<212> TYPE: PRT
<213> ORGANISM: Homo sapiens

<400> SEQUENCE: 5

```
Met Arg Leu Ser Ser Pro Pro Arg Gly Pro Gln Gln Leu Ser Ser
1               5                   10                  15

Phe Gly Ser Val Asp Trp Leu Ser Gln Ser Ser Cys Ser Gly Pro Thr
                20                  25                  30

His Thr Pro Arg Pro Ala Asp Phe Ser Leu Gly Ser Leu Pro Gly Pro
            35                  40                  45

Gly Gln Thr Ser Gly Ala Arg Glu Pro Pro Gln Ala Val Ser Ile Lys
    50                  55                  60

Glu Ala Ala Gly Ser Ser Asn Leu Pro Ala Pro Glu Arg Thr Met Ala
65                  70                  75                  80

Gly Leu Ser Lys Glu Pro Asn Thr Leu Arg Ala Pro Arg Val Arg Thr
                85                  90                  95

Ala Phe Thr Met Glu Gln Val Arg Thr Leu Glu Gly Val Phe Gln His
            100                 105                 110

His Gln Tyr Leu Ser Pro Leu Glu Arg Lys Arg Leu Ala Arg Glu Met
        115                 120                 125

Gln Leu Ser Glu Val Gln Ile Lys Thr Trp Phe Gln Asn Arg Arg Met
    130                 135                 140

Lys His Lys Arg Gln Met Gln Asp Pro Gln Leu His Ser Pro Phe Ser
145                 150                 155                 160

Gly Ser Leu His Ala Pro Pro Ala Phe Tyr Ser Thr Ser Ser Gly Leu
                165                 170                 175

Ala Asn Gly Leu Gln Leu Leu Cys Pro Trp Ala Pro Leu Ser Gly Pro
            180                 185                 190

Gln Ala Leu Met Leu Pro Pro Gly Ser Phe Trp Gly Leu Cys Gln Val
        195                 200                 205

Ala Gln Glu Ala Leu Ala Ser Ala Gly Ala Ser Cys Cys Gly Gln Pro
    210                 215                 220

Leu Ala Ser His Pro Pro Thr Pro Gly Arg Pro Ser Leu Gly Pro Ala
225                 230                 235                 240

Leu Ser Thr Gly Pro Arg Gly Leu Cys Ala Met Pro Gln Thr Gly Asp
                245                 250                 255

Ala Phe
```

<210> SEQ ID NO 6
<211> LENGTH: 777
<212> TYPE: DNA
<213> ORGANISM: Homo sapiens

<400> SEQUENCE: 6

```
atgcgcctct cctcctcccc acctcgtggc ccgcagcagc tctccagctt tggctccgtg      60
```

```
gactggctct cccagagcag ctgctcaggg ccgacccaca ccccaggcc tgccgacttc      120 tccctgggga gcctccctgg cccaggccag acatccggcg cccggagcc cctcaggcc      180 gtcagcatca aggaggccgc cgggtcctca aatctgcctg cgccggagag gaccatggcc     240
gggttgagta aggagccaaa taccttgcgg gcccccgtg tccgcacagc cttcaccatg     300
gagcaggtcc gcaccttgga gggcgtcttc cagcaccacc agtacctgag ccctctggag    360
cggaagaggc tggccaggga gatgcagctc tcagaggtcc agataaaaac ctggtttcag    420
aatcgccgca tgaaacacaa acggcaaatg caggaccccc agctgcacag ccccttctcg    480
gggtctctcc atgcgccccc agctttctac tcaacgtctt ctggccttgc caatggcctg    540
cagctgctgt gcccttgggc acccctgtcc gggcccagg ctctgatgct gcccctggc     600 tccttctggg gtctctgcca agtggcacaa gaggccctgg catctgcggg agcttcctgc    660
tgcgggcagc ctctggcgtc ccaccccct accccaggcc ggccttcgct gggaccagcc    720
ctgtccacgg ggccccgggg cctgtgtgct atgccacaga cggggatgc attttga       777

<210> SEQ ID NO 7
<211> LENGTH: 327
<212> TYPE: PRT
<213> ORGANISM: Homo sapiens

<400> SEQUENCE: 7

Met Thr Lys Ala Phe Ser Ser Val Glu Trp Leu Ala Gln Ser Ser Arg
1               5                   10                  15

Arg Ser His Arg Glu Gln Pro Ser Lys Val Asp Gln Arg Tyr Ser Pro
            20                  25                  30

Tyr Pro Ser Pro Ser Leu Pro Ser Trp Asn Ser Asp Val Ser Pro Ser
        35                  40                  45

Ser Trp Asn Ser Gln Leu Ser Pro Asp Pro Asp Ser Ala Gln Val Ser
    50                  55                  60

Pro Cys Pro Ala Ser Ala Gln Val Ser Pro Tyr Ser Ser Asp Ser Glu
65                  70                  75                  80

Ile Ser Leu Tyr Ser His Glu Glu Ala Ser Phe Tyr Gly Met Asp
            85                  90                  95

Leu Asn Thr Ser Ser Ser Pro Gly Asp Asn Gly Leu Leu His Ser Glu
        100                 105                 110

Met Val Ser Val Pro Asp Asn Ile Pro Arg Ala Ser Ser Asp Glu Asp
    115                 120                 125

Ala Ala Lys Ser Ala Tyr Ser Thr Ser Thr Asp Ser Gly Tyr Glu Ser
    130                 135                 140

Glu Thr Ser Cys Ser Ser Ser Thr Ala Pro Glu Gly Asp Ala Ile Ser
145                 150                 155                 160

Leu Ser Pro Asn Asp Thr Ser Asp Glu Glu Gly Lys Met Gly Arg Arg
            165                 170                 175

Leu Arg Thr Ala Phe Thr Ser Asp Gln Ile Ser Thr Leu Glu Lys Thr
        180                 185                 190

Phe Gln Lys His Arg Tyr Leu Gly Ala Ser Glu Arg Gln Lys Leu Ala
    195                 200                 205

Ala Lys Leu Gln Leu Ser Glu Val Gln Ile Lys Thr Trp Phe Gln Asn
    210                 215                 220

Arg Arg Met Lys Tyr Lys Arg Glu Ile Gln Asp Gly Arg Pro Asp Ser
225                 230                 235                 240

Tyr His Pro Ala Gln Phe Phe Gly Val Tyr Gly Tyr Ala Gln Gln Pro
```

```
                 245                 250                 255
Thr Pro Val Phe Gln His Ala Val Gln His Pro Tyr Pro Gly Tyr Asn
                260                 265                 270
Pro Leu Met Glu Thr Leu Pro Gly Thr Met Pro Tyr Thr Met His Pro
            275                 280                 285
Pro Ala Met Asp Ser Met Thr Pro Phe Asn Ser Gln Pro Phe Gln Met
        290                 295                 300
Leu Tyr Leu Pro Gln Gln His Leu Gly Gln Pro Leu Thr Tyr Gln Glu
305                 310                 315                 320
Glu Arg Pro Phe Val Arg Tyr
                325

<210> SEQ ID NO 8
<211> LENGTH: 987
<212> TYPE: DNA
<213> ORGANISM: Homo sapiens

<400> SEQUENCE: 8
atgactaaag ctttctcctc tgttgaatgg cttgctcaaa gcagccgcag atctcacaga      60
gagcagccaa gcaaagtgga tcagagatat tcaccgtacc ccaggccatc cctgccttcc     120
tggaacagtg atgtgtcccc ttcttcatgg aacagccaac tatctccaga tccagacagt     180
gcccaagtct caccatgccc tgtgagtgca caagtatctc catattcctc agacagtgaa     240
atatcactgt attcacatga agaagaagcc tctttctatg gaatggactt taatacatca     300
tcatcccctg gagacaatgg attgctacac agggacacaa cctcatactc agaggaatg      360 gaggccatgt cggccagcac tccagcaaca tcacctgtga aggggcaca acctgttgat      420 tccgcctaca gcactagcac tgactcaggc tatgaaagtg aaacgagtcg atccaactct     480 acagccctg aaggagatgc ctccgtatct ctgagtccca tgatacctc agatgaagag      540 ggcaagatgg gccgaaggtt gaggacggct ttcaccagtg atcagatctc cactctggag     600
aagacttttc agaaacacag ataccttggg gcgtctgaaa gacggaaact cgcagccaaa     660
ctccagcttt ctgaagtcca gattaaaact tggttccaga accgcaggat gaaatacaaa     720
cgggaaatcc aagatggcag accagactca taccacccag cccagttctt ggtgtgtac      780 ggctatgcac agcagcccac tcctgtattc cagcatgcag tccaacatcc ctacccaggt     840 tataaccac taatggaaac cctgcctggt accatgccct ataccatgca tccacctgcc      900
atggactctc tgactccctt caactctcaa ccttttcaga tgctctacct gccccaacag     960
caccttgggc aacctctggc ctattag                                        987

<210> SEQ ID NO 9
<211> LENGTH: 2428
<212> TYPE: DNA
<213> ORGANISM: Homo sapiens

<400> SEQUENCE: 9
acctggccgc catgcgcctc tcctcctccc cacctcgtgg cccgcagcag ctctccagct      60
ttggctccgt ggactggctc tcccagagca gctgctcagg gccgacccac acccccaggc     120
ctgccgactt ctccctgggg agcctccctg gcccaggcca gacatccggc gcccgggagc     180
cccctcaggc cgtcagcatc aaggaggccg ccgggtcctc aaatctgcct gcgccggaga     240
ggaccatggc cgggttgagt aaggagccaa atacttgcg ggcccccgt gtccgcacag       300 ccttcaccat ggagcaggtc cgcaccttgg agggcgtctt ccagcaccac cagtacctga     360
```

```
gccctctgga gcggaagagg ctggccaggg agatgcagct ctcagaggtc cagataaaaa      420
cctggtttca gaatcgccgc atgaaacaca aacggcaaat gcaggacccc cagctgcaca      480
gccccttctc ggggtctctc catgcgcccc cagctttcta ctcaacgtct tctggccttg      540
ccaatggcct gcagctgctg tgccttgggc accccctgtc cgggcccccag gctctgatgc     600 tgcccctgg ctccttctgg ggtctctgcc aagtggcaca agaggccctg gcatctgcgg       660
gagcttcctg ctgcgggcag cctctggcgt cccacccccc tacccaggcc ggccttcgc      720 tgggaccagc cctgtccacg ggcccccggg gcctgtgtgc tatgccacag acggggatg       780 cattttgagg aggcacctct gactcccaca ctcgcggtct tgctgatcgc acctggctcc      840
tacctggagg actcagttgt tctgtttaca tcctggtggc acctctcacc ctgacccaca      900
caaaggttct ggagattact ggagaatata tataaatata tatatgtacg tatatatgta      960
aatacacata tacgtatata taaatatata tatacatatg tgtgtgtata tatatatata     1020
tttttttttt tttttttttt tttgagacgg agtgttgctc tgtcacccag gctggagtgc     1080
aatgacgcaa tctcggctca ctgcaacctc cgcctcctgg gttcaagcga ttctccagcc     1140
tcagcctccc gagtagctgg gattacagac acccgccacc acgcccggct aattttttct     1200 attttagta gaaatggggt ttcaccatgt tagccaggct ggtctcaaac tcctgaccct      1260
gtgatccgcc cgcctcggcc tcccaaagtg ctgggattac aggcatgagc cactgcaccc     1320
ggccctgaga atatatttat taaagccacc tcttcactga aagttaccga aagagtcggt     1380
ttaggaagga aacgaagggt cagtgaacag agtcaaatgc agaagtgggc ttgtcatggg     1440
tagggctttc ggcgtacgat aaaaggatca tttgttttttt aaaaggggtt ggaaaaactg    1500
gttttccagt tggaaacagt aaaggttgta agctttgtgt gtacaaaaga aaacagggaa     1560
tgcaggtgtg tttatagcgt tgtggttcaa gtccctctta acaagaactc caaagctgga     1620
aagcaggagg gaacaaaggt gaacatgaag gcgaggatgc tggggccctg cagtgcgctc     1680
taggctgtgc gtgagccggg actgtaccca cagcttgctg agggctgctc ttcttgggcc     1740
agggaaagca gggcagccgg gacctgcggc tgtgcctgga ctgaagctgt cccgcaggtc     1800
cccaccctcc aacacgtgct cacctgtccc cctcctcgca gcagcctcgg gacaaaacaa     1860
tgactcaagg acagcacttc tcgcagaagg tctggaagtg cccagaatgg gaggcacgga     1920
agcccctccc ggggaggact cccgcgttga tggaccgttc ttggtgcaga ctcctgactg     1980
cgtgcatgaa acctgagaca agtgcaattc cttccatgtc gccccagagt gcccaggagg     2040
caggcagtgc ggggtgccca ggcagacggg ttcagcctgc agaactggag gcgacctgtg     2100
aaacccaccc gggcacccca acaggaacag aagcgtggtc ctgcggctgc gtccccagcg     2160
agtttcactt tccccttgct cgtttctccc ttgttgtaag tgtttacaac tggcatgtgc     2220
ttttaaacgt caggtaagag gggaacagct gctgtacatc gtcctggcga gtgacaatgt     2280
gacagaagcc tggcgaggc cctcggaggg cagcagctgg acaggggcta ctgggtttgg     2340
cctggacagc actgatttgt ggatgtggat ggggcacgt tgtccgtgat aaaagtacaa      2400
gtgcccctca caaaaaaaaa aaaaaaaa                                        2428
```

<210> SEQ ID NO 10
<211> LENGTH: 1281
<212> TYPE: DNA
<213> ORGANISM: Homo sapiens

<400> SEQUENCE: 10

```
agaacacaag gactaataca gacaagatga ctaaagcttt ctcctctgtt gaatggcttg       60
```

```
ctcaaagcag ccgcagatct cacagagagc agccaagcaa agtggatcag agatattcac    120
cgtaccccag gccatccctg ccttcctgga acagtgatgt gtccccttct tcatggaaca    180
gccaactatc tccagatcca gacagtgccc aagtctcacc atgccctgtg agtgcacaag    240
tatctccata ttcctcagac agtgaaatat cactgtattc acatgaagaa gaagcctctt    300
tctatggaat ggactttaat acatcatcat ccoctggaga caatggattg ctacacaggg    360
acacaacctc atactccaga ggaatggagg ccatgtcggc cagcactcca gcaacatcac    420
ctgtgaaagg ggcacaacct gttgattccg cctacagcac tagcactgac tcaggctatg    480
aaagtgaaac gagtcgatcc aactctacag cccctgaagg agatgcctcc gtatctctga    540
gtcccaatga tacctcagat gaagagggca agatgggccg aaggttgagg acggctttca    600
ccagtgatca gatctccact ctggagaaga cttttcagaa acacagatac cttggggcgt    660
ctgaaagacg gaaactcgca gccaaactcc agctttctga agtccagatt aaaacttggt    720
tccagaaccg caggatgaaa tacaaacggg aaatccaaga tggcagacca gactcatacc    780
acccagccca gttctttggt gtgtacggct atgcacagca gcccactcct gtattccagc    840
atgcagtcca acatccctac ccaggttata acccactaat ggaaaccctg cctggtacca    900
tgccctatac catgcatcca cctgccatgg actctctgac tcccttcaac tctcaacctt    960
ttcagatgct ctacctgccc caacagcacc ttgggcaacc tctggcctat taggaagaaa   1020
ggccatttgt tagatattaa tctagaactt ataaaaggac tatactaaag gctggacttt   1080
tccatggact tctgtcctcc cgcaggacaa acaaaattgc actgaatatt gttattgaca   1140
agatgtttac tgaatggatg gctaatattg ggccatgtgt tgacatgatt ttattcacat   1200
tgaatagtgg cgtgtatatt ctatgaaaaa taccatttat atgactaata aatgtaagtt   1260
atatttaaaa aaaaaaaaaa a                                             1281
```

<210> SEQ ID NO 11
<211> LENGTH: 271
<212> TYPE: PRT
<213> ORGANISM: Homo sapiens

<400> SEQUENCE: 11

```
Pro Asp Pro Asp Ser Ala Gln Val Ser Pro Cys Pro Ala Ser Ala Gln
1               5                   10                  15

Val Ser Pro Tyr Ser Ser Asp Ser Glu Ile Ser Leu Tyr Ser His Glu
            20                  25                  30

Glu Glu Ala Ser Phe Tyr Gly Met Asp Leu Asn Thr Ser Ser Ser Pro
        35                  40                  45

Gly Asp Asn Gly Leu Leu His Ser Glu Met Val Ser Val Pro Asp Asn
    50                  55                  60

Ile Pro Arg Ala Ser Ser Asp Glu Asp Ala Ala Lys Ser Ala Tyr Ser
65                  70                  75                  80

Thr Ser Thr Asp Ser Gly Tyr Glu Ser Glu Thr Ser Cys Ser Ser Ser
                85                  90                  95

Thr Ala Pro Glu Gly Asp Ala Ile Ser Leu Ser Pro Asn Asp Thr Ser
            100                 105                 110

Asp Glu Glu Gly Lys Met Gly Arg Arg Leu Arg Thr Ala Phe Thr Ser
        115                 120                 125

Asp Gln Ile Ser Thr Leu Glu Lys Thr Phe Gln Lys His Arg Tyr Leu
    130                 135                 140

Gly Ala Ser Glu Arg Gln Lys Leu Ala Ala Lys Leu Gln Leu Ser Glu
```

```
145                 150                 155                 160
Val Gln Ile Lys Thr Trp Phe Gln Asn Arg Arg Met Lys Tyr Lys Arg
                165                 170                 175

Glu Ile Gln Asp Gly Arg Pro Asp Ser Tyr His Pro Ala Gln Phe Phe
                180                 185                 190

Gly Val Tyr Gly Tyr Ala Gln Gln Pro Thr Pro Val Phe Gln His Ala
                195                 200                 205

Val Gln His Pro Tyr Pro Gly Tyr Asn Pro Leu Met Glu Thr Leu Pro
        210                 215                 220

Gly Thr Met Pro Tyr Thr Met His Pro Pro Ala Met Asp Ser Met Thr
225                 230                 235                 240

Pro Phe Asn Ser Gln Pro Phe Gln Met Leu Tyr Leu Pro Gln Gln His
                245                 250                 255

Leu Gly Gln Pro Leu Thr Tyr Gln Glu Glu Arg Pro Phe Val Arg
                260                 265                 270

<210> SEQ ID NO 12
<211> LENGTH: 151
<212> TYPE: PRT
<213> ORGANISM: Homo sapiens

<400> SEQUENCE: 12

Arg Leu Arg Thr Ala Phe Thr Ser Asp Gln Ile Ser Thr Leu Glu Lys
1               5                   10                  15

Thr Phe Gln Lys His Arg Tyr Leu Gly Ala Ser Glu Arg Gln Lys Leu
                20                  25                  30

Ala Ala Lys Leu Gln Leu Ser Glu Val Gln Ile Lys Thr Trp Phe Gln
                35                  40                  45

Asn Arg Arg Met Lys Tyr Lys Arg Glu Ile Gln Asp Gly Arg Pro Asp
        50                  55                  60

Ser Tyr His Pro Ala Gln Phe Phe Gly Val Tyr Gly Tyr Ala Gln Gln
65              70                  75                  80

Pro Thr Pro Val Phe Gln His Ala Val Gln His Pro Tyr Pro Gly Tyr
                85                  90                  95

Asn Pro Leu Met Glu Thr Leu Pro Gly Thr Met Pro Tyr Thr Met His
                100                 105                 110

Pro Pro Ala Met Asp Ser Met Thr Pro Phe Asn Ser Gln Pro Phe Gln
                115                 120                 125

Met Leu Tyr Leu Pro Gln Gln His Leu Gly Gln Pro Leu Thr Tyr Gln
                130                 135                 140

Glu Glu Arg Pro Phe Val Arg
145                 150

<210> SEQ ID NO 13
<211> LENGTH: 181
<212> TYPE: PRT
<213> ORGANISM: Homo sapiens

<400> SEQUENCE: 13

Met Thr Lys Ala Phe Ser Ser Val Glu Trp Leu Ala Gln Ser Ser Arg
1               5                   10                  15

Arg Ser His Arg Glu Gln Pro Ser Lys Val Asp Gln Arg Tyr Ser Pro
                20                  25                  30

Tyr Pro Ser Pro Ser Leu Pro Ser Trp Asn Ser Asp Val Ser Pro Ser
                35                  40                  45

Ser Trp Asn Ser Gln Leu Ser Pro Asp Pro Asp Ser Ala Gln Val Ser
```

```
                  50                  55                  60
Pro Cys Pro Ala Ser Ala Gln Val Ser Pro Tyr Ser Ser Asp Ser Glu
 65                  70                  75                  80

Ile Ser Leu Tyr Ser His Glu Glu Ala Ser Phe Tyr Gly Met Asp
                     85                  90                  95

Leu Asn Thr Ser Ser Ser Pro Gly Asp Asn Gly Leu Leu His Ser Glu
                    100                 105                 110

Met Val Ser Val Pro Asp Asn Ile Pro Arg Ala Ser Ser Asp Glu Asp
                115                 120                 125

Ala Ala Lys Ser Ala Tyr Ser Thr Ser Thr Asp Ser Gly Tyr Glu Ser
                130                 135                 140

Glu Thr Ser Cys Ser Ser Ser Thr Ala Pro Glu Gly Asp Ala Ile Ser
145                 150                 155                 160

Leu Ser Pro Asn Asp Thr Ser Asp Glu Glu Gly Lys Met Gly Arg Arg
                    165                 170                 175

Leu Arg Thr Ala Phe
                180

<210> SEQ ID NO 14
<211> LENGTH: 241
<212> TYPE: PRT
<213> ORGANISM: Homo sapiens

<400> SEQUENCE: 14

Met Thr Lys Ala Phe Ser Ser Val Glu Trp Leu Ala Gln Ser Ser Arg
 1               5                  10                  15

Arg Ser His Arg Glu Gln Pro Ser Lys Val Asp Gln Arg Tyr Ser Pro
                 20                  25                  30

Tyr Pro Ser Pro Ser Leu Pro Ser Trp Asn Ser Asp Val Ser Pro Ser
                 35                  40                  45

Ser Trp Asn Ser Gln Leu Ser Pro Asp Pro Asp Ser Ala Gln Val Ser
             50                  55                  60

Pro Cys Pro Ala Ser Ala Gln Val Ser Pro Tyr Ser Ser Asp Ser Glu
 65                  70                  75                  80

Ile Ser Leu Tyr Ser His Glu Glu Ala Ser Phe Tyr Gly Met Asp
                     85                  90                  95

Leu Asn Thr Ser Ser Ser Pro Gly Asp Asn Gly Leu Leu His Ser Glu
                    100                 105                 110

Met Val Ser Val Pro Asp Asn Ile Pro Arg Ala Ser Ser Asp Glu Asp
                115                 120                 125

Ala Ala Lys Ser Ala Tyr Ser Thr Ser Thr Asp Ser Gly Tyr Glu Ser
                130                 135                 140

Glu Thr Ser Cys Ser Ser Ser Thr Ala Pro Glu Gly Asp Ala Ile Ser
145                 150                 155                 160

Leu Ser Pro Asn Asp Thr Ser Asp Glu Glu Gly Lys Met Gly Arg Arg
                    165                 170                 175

Leu Arg Thr Ala Phe Thr Ser Asp Gln Ile Ser Thr Leu Glu Lys Thr
                180                 185                 190

Phe Gln Lys His Arg Tyr Leu Gly Ala Ser Glu Arg Gln Lys Leu Ala
                195                 200                 205

Ala Lys Leu Gln Leu Ser Glu Val Gln Ile Lys Thr Trp Phe Gln Asn
                210                 215                 220

Arg Arg Met Lys Tyr Lys Arg Glu Ile Gln Asp Gly Arg Pro Asp Ser
225                 230                 235                 240
```

Tyr

<210> SEQ ID NO 15
<211> LENGTH: 216
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Thr Lys Ala Phe Ser Ser Val Glu Trp Leu Ala Gln Ser Ser Arg
1               5                   10                  15

Arg Ser His Arg Glu Gln Pro Ser Lys Val Asp Gln Arg Tyr Ser Pro
                20                  25                  30

Tyr Pro Ser Pro Ser Leu Pro Ser Trp Asn Ser Asp Val Ser Pro Ser
            35                  40                  45

Ser Trp Asn Ser Gln Leu Ser Pro Asp Pro Asp Ser Ala Gln Val Ser
        50                  55                  60

Pro Cys Pro Ala Ser Ala Gln Val Ser Pro Tyr Ser Ser Asp Ser Glu
65                  70                  75                  80

Ile Ser Leu Tyr Ser His Glu Glu Ala Ser Phe Tyr Gly Met Asp
                85                  90                  95

Leu Asn Thr Ser Ser Ser Pro Gly Asp Asn Gly Leu Leu His Ser Glu
                100                 105                 110

Met Val Ser Val Pro Asp Asn Ile Pro Arg Ala Ser Ser Asp Glu Asp
            115                 120                 125

Ala Ala Tyr His Pro Ala Gln Phe Phe Gly Val Tyr Gly Tyr Ala Gln
        130                 135                 140

Gln Pro Thr Pro Val Phe Gln His Ala Val Gln His Pro Tyr Pro Gly
145                 150                 155                 160

Tyr Asn Pro Leu Met Glu Thr Leu Pro Gly Thr Met Pro Tyr Thr Met
                165                 170                 175

His Pro Pro Ala Met Asp Ser Met Thr Pro Phe Asn Ser Gln Pro Phe
                180                 185                 190

Gln Met Leu Tyr Leu Pro Gln Gln His Leu Gly Gln Pro Leu Thr Tyr
            195                 200                 205

Gln Glu Glu Arg Pro Phe Val Arg
        210                 215

<210> SEQ ID NO 16
<211> LENGTH: 341
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Thr Lys Ala Phe Ser Ser Val Glu Trp Leu Ala Gln Ser Ser Arg
1               5                   10                  15

Arg Ser His Arg Glu Gln Pro Ser Lys Val Asp Gln Arg Tyr Ser Pro
                20                  25                  30

Tyr Pro Ser Pro Ser Leu Pro Ser Trp Asn Ser Asp Val Ser Pro Ser
            35                  40                  45

Ser Trp Asn Ser Gln Leu Ser Pro Asp Pro Asp Ser Ala Gln Val Ser
        50                  55                  60

Pro Cys Pro Ala Ser Ala Gln Val Ser Pro Tyr Ser Ser Asp Ser Glu

-continued

```
                65                  70                  75                  80
Ile Ser Leu Tyr Ser His Glu Glu Ala Ser Phe Tyr Gly Met Asp
                85                  90                  95
Leu Asn Thr Ser Ser Ser Pro Gly Asp Asn Gly Leu Leu His Ser Glu
               100                 105                 110
Met Val Ser Val Pro Asp Asn Ile Pro Arg Ala Ser Ser Asp Glu Asp
               115                 120                 125
Ala Ala Lys Ser Ala Tyr Ser Thr Ser Thr Asp Ser Gly Tyr Glu Ser
           130                 135                 140
Glu Thr Ser Cys Ser Ser Ser Thr Ala Pro Glu Gly Asp Ala Ile Ser
145                 150                 155                 160
Leu Ser Pro Asn Asp Thr Ser Asp Glu Glu Gly Lys Met Gly Arg Arg
                   165                 170                 175
Val Arg Thr Ala Phe Thr Met Glu Gln Val Arg Thr Leu Glu Gly Val
               180                 185                 190
Phe Gln His His Gln Tyr Leu Ser Pro Leu Glu Arg Lys Arg Leu Ala
               195                 200                 205
Arg Glu Met Gln Leu Ser Glu Val Gln Ile Lys Thr Trp Phe Gln Asn
           210                 215                 220
Arg Arg Met Lys His Lys Arg Gln Met Gln Asp Pro Gln Leu His Ser
225                 230                 235                 240
Pro Phe Ser Gly Ser Leu His Ala Pro Pro Ala Phe Tyr Ser Thr Ser
                   245                 250                 255
Ser Gly Leu Ala Asn Gly Leu Gln Leu Leu Cys Pro Trp Ala Pro Leu
               260                 265                 270
Ser Gly Pro Gln Ala Leu Met Leu Pro Pro Gly Ser Phe Trp Gly Leu
           275                 280                 285
Cys Gln Val Ala Gln Glu Ala Leu Ala Ser Ala Gly Ala Ser Cys Cys
           290                 295                 300
Gly Gln Pro Leu Ala Ser His Pro Pro Thr Pro Gly Arg Pro Ser Leu
305                 310                 315                 320
Gly Pro Ala Leu Ser Thr Gly Pro Arg Gly Leu Cys Ala Met Pro Gln
                   325                 330                 335
Thr Gly Asp Ala Phe
               340

<210> SEQ ID NO 17
<211> LENGTH: 11
<212> TYPE: PRT
<213> ORGANISM: Artificial Sequence
<220> FEATURE:
<223> OTHER INFORMATION: Synthetic peptide

<400> SEQUENCE: 17

Thr Asp Ser Gly Tyr Glu Ser Glu Thr Ser Cys
1               5                   10
```